(12) United States Patent
Martin et al.

(10) Patent No.: US 7,915,232 B2
(45) Date of Patent: Mar. 29, 2011

(54) 4'-SUBSTITUTED NUCLEOSIDE DERIVATIVES AS INHIBITORS OF HCV RNA REPLICATION

(75) Inventors: Joseph Armstrong Martin, Menlo Park, CA (US); John Herbert Merrett, Baldock (GB); Isabel Najera, Menlo Park, CA (US); Rene Robert Devos, Welwyn Garden City (GB); Christopher John Hobbs, Hertford (GB); Wen Rong Jiang, Redwood City, CA (US); Nobuo Shimma, Chigasaki (JP); Takuo Tsukuda, Odawara (JP)

(73) Assignee: Roche Palo Alto LLC, South San Francisco, CA (US)

( * ) Notice: Subject to any disclaimer, the term of this patent is extended or adjusted under 35 U.S.C. 154(b) by 0 days.

(21) Appl. No.: 12/559,186

(22) Filed: Sep. 14, 2009

(65) Prior Publication Data

US 2010/0004192 A1 Jan. 7, 2010

Related U.S. Application Data

(60) Continuation of application No. 10/891,967, filed on Jul. 15, 2004, now Pat. No. 7,608,801, which is a division of application No. 10/167,106, filed on Jun. 11, 2002, now Pat. No. 6,784,166.

(30) Foreign Application Priority Data

Jun. 12, 2001 (GB) .................................. 0114286.8

(51) Int. Cl.
*A61K 31/70* (2006.01)
*C07H 19/167* (2006.01)
*C07H 19/20* (2006.01)

(52) U.S. Cl. ............... 514/45; 514/46; 514/47; 514/48; 536/26.23; 536/26.26; 536/26.7; 536/27.21; 536/27.6; 536/27.61; 536/27.62; 536/27.8; 536/27.81

(58) Field of Classification Search .................. None
See application file for complete search history.

(56) References Cited

U.S. PATENT DOCUMENTS

| 3,910,885 | A | 10/1975 | Moffatt et al. | |
|---|---|---|---|---|
| 5,155,112 | A | 10/1992 | Storer | |
| 5,496,546 | A | 3/1996 | Wang | |
| 6,333,315 | B1 * | 12/2001 | Ohrui et al. | 514/45 |
| 6,403,568 | B1 * | 6/2002 | Ohrui et al. | 514/49 |
| 6,784,166 | B2 * | 8/2004 | Devos et al. | 514/47 |
| 7,608,601 | B2 * | 10/2009 | Devos et al. | 514/46 |

FOREIGN PATENT DOCUMENTS

WO    WO98/16184 A2 *  4/1998

OTHER PUBLICATIONS

Hai et al. (I), Species- or Isozyme-Specific Enzyme Inhibitors. 9. Selective Effects in Inhibitions of Rat Pyruvate Kinase Isozymes by Adenosine 5'-Diphosphate Derivatives, Journal of Medicinal Chemistry, 25(10), 1184-1188 (1982).*

Hai et al. (II), Species- or Isozyme-Specific Enzyme Inhibitors. 7. Selective Effects in Inhibitions of Rat Pyruvate Kinase Isozymes by Adenosine 5'-Diphosphate Derivatives, Journal of Medicinal Chemistry, 25(7), 806-812 (1982).*

Hans Maag, et al., "Synthesis and Anti-HIV Activity of 4'-Azido- and 4'-Methoxynucleosides[1]", *Journal of Med. Chem.*, (1992), pp. 1440-1451, vol. 35.

J. G. Moffatt, outline of the synthesis of 4'-azidocytidine from chapter titled "Chemical Transformations of the Sugar Moiety of Nucleosides," from book *Nucleoside Analogues*, (1979) p. 144 published by Plenum Press, New York and London.

* cited by examiner

*Primary Examiner* — Lawrence E Crane
(74) *Attorney, Agent, or Firm* — Brian L. Buckwalter

(57) ABSTRACT

The present invention relates to the use of nucleoside derivatives of formula Ia

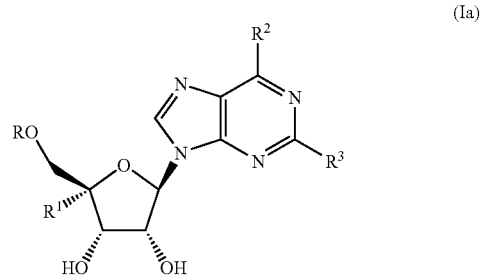

(Ia)

wherein the symbols are as defined in the specification, and of pharmaceutically acceptable salts thereof which inhibit HCV polymerase and are useful for treating a patient suffering from a HCV infection and to pharmaceutical compositions containing such compounds.

2 Claims, No Drawings

4'-SUBSTITUTED NUCLEOSIDE DERIVATIVES AS INHIBITORS OF HCV RNA REPLICATION

CROSS REFERENCE TO RELATED APPLICATIONS

This application is a continuation of U.S. Ser. No. 10/891,967 filed Jul. 15, 2004, now issued as U.S. Pat. No. 7,608,801 on Oct. 27, 2009, which is a divisional of Ser. No. 10/167,106, filed Jun. 11, 2002, now issued as U.S. Pat. No. 6,784,166 granted Aug. 31, 2004, which claims benefit under Title 35, United States Code, §119 of Great Britain Patent Application No. 00114286.8, filed on Jun. 12, 2001.

BACKGROUND OF THE INVENTION

The invention relates to nucleoside derivatives as inhibitors of HCV replicon RNA replication. In particular, the invention is concerned with the use of purine and pyrimidine nucleoside derivatives as inhibitors of subgenomic Hepatitis C Virus (HCV) RNA replication and pharmaceutical compositions containing such compounds.

Hepatitis C virus is the leading cause of chronic liver disease throughout the world. Patients infected with HCV are at risk of developing cirrhosis of the liver and subsequent hepatocellular carcinoma and hence HCV is the major indication for liver transplantation. Only two approved therapies are currently available for the treatment of HCV infection (R. G. Gish, Sem. Liver. Dis., 1999, 19, 35). These are interferon-α monotherapy and, more recently, combination therapy of the nucleoside analogue, ribavirin (Virazole), with interferon-α.

Many of the drugs approved for the treatment of viral infections are nucleosides or nucleoside analogues and most of these nucleoside analogue drugs inhibit viral replication, following conversion to the corresponding triphosphates, through inhibition of the viral polymerase enzymes. This conversion to the triphosphate is commonly mediated by cellular kinases and therefore the direct evaluation of nucleosides as inhibitors of HCV replication is only conveniently carried out using a cell-based assay. For HCV the availability of a true cell-based viral replication assay or animal model of infection is lacking.

Hepatitis C virus belongs to the family of Flaviridae. It is an RNA virus, the RNA genome encoding a large polyprotein which after processing produces the necessary replication machinery to ensure synthesis of progeny RNA. It is believed that most of the non-structural proteins encoded by the HCV RNA genome are involved in RNA replication. Lohmann et al. [V. Lohmann et al., Science, 1999, 285, 110-113] have described the construction of a Human Hepatoma (Huh7) cell line in which subgenomic HCV RNA molecules have been introduced and shown to replicate with high efficiency. It is believed that the mechanism of RNA replication in these cell lines is identical to the replication of the full length HCV RNA genome in infected hepatocytes. The subgenomic HCV cDNA clones used for the isolation of these cell lines have formed the basis for the development of a cell-based assay for identifying nucleoside analogue inhibitors of HCV replication.

SUMMARY OF THE INVENTION

The invention is concerned with the use of compounds of the formula Ia wherein

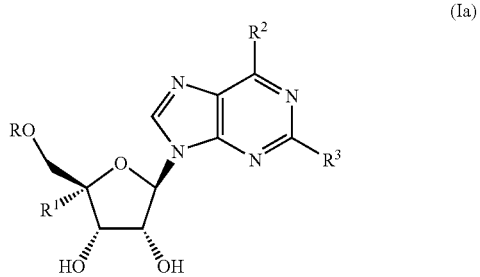

(Ia)

the compound is in the D configuration;
R is hydrogen or —[P(O)(OH)]—O]$_n$H and n is 1, 2 or 3
$R^1$ is —N$_3$, C$_{3-6}$ alkenyl, C$_{3-6}$ alkynyl, C$_{2-6}$ alkoxy;
$R^2$ and $R^3$ are independently hydrogen, —OH or —NR$^4{}_2$;
$R^4$ is hydrogen or C$_{1-3}$ alkyl;
or a pharmaceutically acceptable salt thereof.
for the treatment of diseases mediated by the Hepatitis C Virus (HCV) and for pharmaceutical compositions comprising such compounds.

DETAILED DESCRIPTION OF THE INVENTION

The compounds of formula I have been shown to be inhibitors of subgenomic Hepatitis C Virus replication in a hepatoma cell line. These compounds have the potential to be efficacious as antiviral drugs for the treatment of HCV infections in human.

In compounds, wherein R is a phosphate group —[P(O)(OH)—O]$_n$H, n is preferably 1. The phosphate group may be in the form of a stabilized monophosphate prodrug or other pharmaceutically acceptable leaving group which when administered in vivo, is capable of providing a compound wherein R is monophosphate. These "pronucleotides" can improve the properties such as activity, bioavailability or stability of the parent nucleotide.

Examples of substituent groups which can replace one or more of the hydrogens in the phosphate moiety are described in C. R. Wagner et al., Medicinal Research Reviews, 2000, 20(6), 417 or in R. Jones and N. Bischofberger, Antiviral Research 1995, 27, 1. Such pronucleotides include alkyl and aryl phosphodiesters, steroid phosphodiesters, alkyl and aryl phosphotriesters, cyclic alkyl phosphotriesters, cyclosaligenyl (CycloSal) phosphotriesters, S-acyl-2-thioethyl (SATE) derivatives, dithioethyl (DTE) derivatives, pivaloyloxymethyl phosphoesters, para-acyloxybenzyl (PAOB) phosphoesters, glycerolipid phosphodiesters, glycosyl lipid phosphotriesters, dinucleosidyl phosphodiesters, dinucleoside phosphotriesters, phosphorodiamidates, cyclic phosphoramidates, phosphoramidate monoesters and phosphoramidate diesters.

The invention also includes pro-drugs or bioprecursors of the parent nucleoside which are converted in vivo to the compound of formula I wherein R is hydrogen, or at least one of $R^2$, $R^3$ and $R^4$ is hydroxy. Preferred pro-drug derivatives include carboxylic esters in which the non-carbonyl moiety of the ester group is selected from straight or branched alkyl (e.g. methyl, n-propyl, n-butyl or tert.-butyl), alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy or amino); sulphonate esters such as alkylsulphonyl or arylsulphonyl (e.g. methanesulphonyl); amino acid esters (e.g. L-valyl or L-isoleucyl) or pharmaceutically acceptable salts thereof. The preparation is carried out according to known methods in the art, for example methods known from textbooks on organic chemistry (e.g. from J. March (1992), "Advanced Organic Chemistry: Reactions, Mechanisms, and Structure", $4^{th}$ ed. John Wiley & Sons).

The term "alkyl" as used herein denotes a straight or branched chain hydrocarbon residue containing 1 to 12 carbon atoms. Preferably, the term "alkyl" denotes a straight or branched chain hydrocarbon residue containing 1 to 7 carbon atoms. Most preferred are methyl, ethyl, propyl, isopropyl, n-butyl, isobutyl, tert.-butyl or pentyl. The alkyl may be unsubstituted or substituted. The substituents are selected from one or more of cycloalkyl, nitro, amino, alkyl amino, dialkyl amino, alkyl carbonyl and cycloalkyl carbonyl.

The term "cycloalkyl" as used herein denotes an optionally substituted cycloalkyl group containing 3 to 7 carbon atoms, e.g. cyclopropyl, cyclobutyl, cyclopentyl, cyclohexyl or cycloheptyl.

The term "alkoxy" as used herein denotes an optionally substituted straight or branched chain alkyl-oxy group wherein the "alkyl" portion is as defined above such as methoxy, ethoxy, n-propyloxy, i-propyloxy, n-butyloxy, i-butyloxy, tert.-butyloxy, pentyloxy, hexyloxy, heptyloxy including their isomers.

The term "alkoxyalkyl" as used herein denotes an alkoxy group as defined above which is bonded to an alkyl group as defined above. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, tert.-butyloxybutyl, methoxypentyl, ethoxypentyl, propyloxypentyl including their isomers.

The term "alkenyl" as used herein denotes an unsubstituted or substituted hydrocarbon chain radical having from 2 to 7 carbon atoms, preferably from 2 to 4 carbon atoms, and having one or two olefinic double bonds, preferably one olefinic double bond. Examples are vinyl, 1-propenyl, 2-propenyl(allyl) or 2-butenyl(crotyl).

The term "alkynyl" as used herein denotes to unsubstituted or substituted hydrocarbon chain radical having from 2 to 7 carbon atoms, preferably 2 to 4 carbon atoms, and having one or where possible two triple bonds, preferably one triple bond. Examples are ethynyl, 1-propynyl, 2-propynyl, 1-butynyl, 2-butynyl or 3-butynyl.

The term "hydroxyalkyl" as used herein denotes a straight or branched chain alkyl group as defined above wherein 1, 2, 3 or more hydrogen atoms are substituted by a hydroxy group. Examples are hydroxymethyl, 1-hydroxyethyl, 2-hydroxyethyl, 1-hydroxypropyl, 2-hydroxypropyl, 3-hydroxypropyl, hydroxyisopropyl, hydroxybutyl and the like.

The term "haloalkyl" as used herein denotes a straight or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl and the like.

The term "alkylthio" as used herein denotes a straight or branched chain (alkyl)S— group wherein the "alkyl" portion is as defined above. Examples are methylthio, ethylthio, n-propylthio, i-propylthio, n-butylthio, i-butylthio or tert.-butylthio.

The term "aryl" as used herein denotes an optionally substituted phenyl and naphthyl (e. g. 1-naphthyl, 2-naphthyl or 3-naphthyl). Suitable substituents for aryl can be selected from those named for alkyl, in addition however, halogen, hydroxy and optionally substituted alkyl, haloalkyl, alkenyl, alkynyl and aryloxy are substituents which can be added to the selection.

The term "heterocyclyl" as used herein denotes an optionally substituted saturated, partially unsaturated or aromatic monocyclic, bicyclic or tricyclic heterocyclic systems which contain one or more hetero atoms selected from nitrogen, oxygen and sulfur which can also be fused to an optionally substituted saturated, partially unsaturated or aromatic monocyclic carbocycle or heterocycle.

Examples of suitable heterocycles are oxazolyl, isoxazolyl, furyl, tetrahydrofuryl, 1,3-dioxolanyl, dihydropyranyl, 2-thienyl, 3-thienyl, pyrazinyl, isothiazolyl, dihydrooxazolyl, pyrimidinyl, tetrazolyl, 1-pyrrolidinyl, 2-pyrrolidinyl, 3-pyrrolidinyl, pyrrolidinonyl, (N-oxide)-pyridinyl, 1-pyrrolyl, 2-pyrrolyl, triazolyl e.g. 1,2,3-triazolyl or 1,2,4-triazolyl, 1-pyrazolyl, 2-pyrazolyl, 4-pyrazolyl, piperidinyl, morpholinyl (e.g. 4-morpholinyl), thiomorpholinyl (e.g. 4-thiomorpholinyl), thiazolyl, pyridinyl, dihydrothiazolyl, imidazolidinyl, pyrazolinyl, piperazinyl, 1-imidazolyl, 2-imidazolyl, 4-imidazolyl, thiadiazolyl e. g. 1,2,3-thiadiazolyl, 4-methylpiperazinyl, 4-hydroxypiperidin-1-yl.

Suitable substituents for heterocyclyl can be selected from those named for alkyl, in addition however, optionally substituted alkyl, alkenyl, alkynyl, an oxo group (=O) or aminosulphonyl are substituents which can be added to the selection.

The term "acyl" ("alkylcarbonyl") as used herein denotes a group of formula C(=O)R wherein R is hydrogen, an unsubstituted or substituted straight or branched chain hydrocarbon residue containing 1 to 7 carbon atoms or a phenyl group. Most preferred acyl groups are those wherein R is hydrogen, an unsubstituted straight chain or branched hydrocarbon residue containing 1 to 4 carbon atoms or a phenyl group.

The term halogen stands for fluorine, chlorine, bromine or iodine, preferable fluorine, chlorine, bromine.

Within the invention the term "X" represents O, S or $CH_2$, preferably O or $CH_2$. Most preferred "X" represents O.

Within the invention the term "Z" represents O or S, preferably O.

In the pictorial representation of the compounds given throughout this application, a thickened tapered line (—) indicates a substituent which is above the plane of the ring to which the asymmetric carbon belongs and a dotted line (·····) indicates a substituent which is below the plane of the ring to which the asymmetric carbon belongs.

Compounds of formula I exhibit stereoisomerism. These compounds can be any isomer of the compound of formula I or mixtures of these isomers. The compounds and intermediates of the present invention having one or more asymmetric carbon atoms may be obtained as racemic mixtures of stereoisomers which can be resolved.

Compounds of formula I exhibit tautomerism that means that the compounds of this invention can exist as two or more chemical compounds that are capable of facile interconversion. In many cases it merely means the exchange of a hydrogen atom between two other atoms, to either of which it forms a covalent bond. Tautomeric compounds exist in a mobile equilibrium with each other, so that attempts to prepare the separate substances usually result in the formation of a mixture that shows all the chemical and physical properties to be expected on the basis of the structures of the components.

The most common type of tautomerism is that involving carbonyl, or keto, compounds and unsaturated hydroxyl compounds, or enols. The structural change is the shift of a hydrogen atom between atoms of carbon and oxygen, with the rearrangement of bonds. For example, in many aliphatic aldehydes and ketones, such as acetaldehyde, the keto form is the predominant one; in phenols, the enol form is the major component.

Compounds of formula I which are basic can form pharmaceutically acceptable salts with inorganic acids such as hydrohalic acids (e.g. hydrochloric acid and hydrobromic acid), sulphuric acid, nitric acid and phosphoric acid, and the like, and with organic acids (e.g. with acetic acid, tartaric acid, succinic acid, fumaric acid, maleic acid, malic acid, salicylic acid, citric acid, methanesulphonic acid and p-toluene sulphonic acid, and the like). The formation and isolation of such salts can be carried out according to methods known in the art.

Preferred is the use of compounds of formula I, wherein

R is hydrogen;

$R^1$ is alkyl, alkenyl, alkynyl, haloalkyl, alkylcarbonyl, alkoxy, hydroxymethyl, cyano, azido, alkoxyiminomethyl, alkylcarbonylamino, alkylaminomethyl or dialkylaminomethyl;

$R^2$ is hydrogen, hydroxy, alkoxy or halogen;

$R^3$ and $R^4$ are hydrogen, hydroxy, alkoxy, halogen or hydroxyalkyl, provided that at least one of $R^3$ and $R^4$ is hydrogen; or $R^3$ and $R^4$ represent fluorine;

X is O or $CH_2$; and

B signifies a 9-purinyl residue B1 or a 1-pyrimidyl residue B2 as defined above.

Examples of preferred compounds are listed below

| Compound no. | STRUCTURE | Name |
|---|---|---|
| compound 6 | 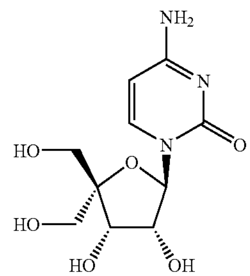 | 4'-C-(Hydroxymethyl)cytidine |
| compound 7 | 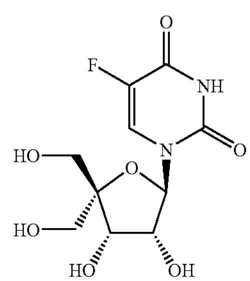 | 5-Fluoro-4'-C-(hydroxymethyl)-uridine |
| compound 8 | 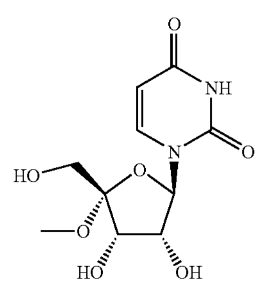 | 4'-C-Methoxyuridine |
| compound 10 | 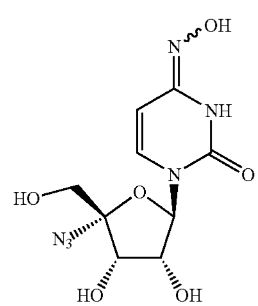 | (E and/or Z)-4'-C-Azidouridine-4-oxime |

-continued

| Compound no. | STRUCTURE | Name |
| --- | --- | --- |
| compound 11 | 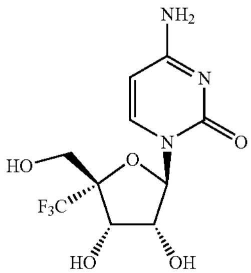 | 4'-C-(Trifluoromethyl)cytidine |
| compound 12 | 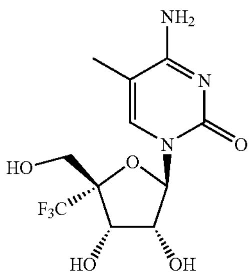 | 4'-C-(Trifluoromethyl)-5-methyl-cytidine |
| compound 13 | 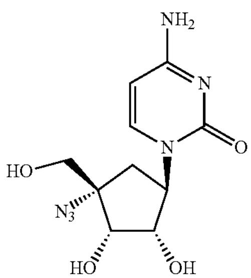 | 1-[4(S)-Azido-2(S),3(R)-dihydroxy-4-(hydroxymethyl)-1(R)-cyclopentyl]cytosine |
| compound 14 | 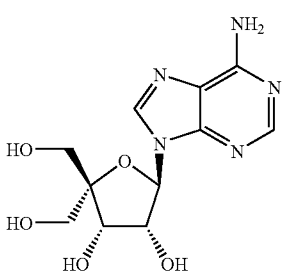 | 4'-C-(Hydroxymethyl)adenosine |
| compound 15 | 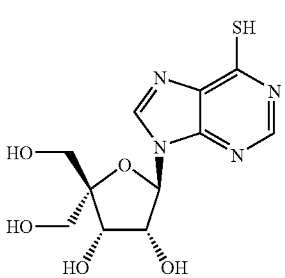 | 9-[4-C-(Hydroxymethyl)-beta-D-ribofuranosyl]-6-mercaptopurine |

-continued
| Compound no. | STRUCTURE | Name |
|---|---|---|
| compound 16 | 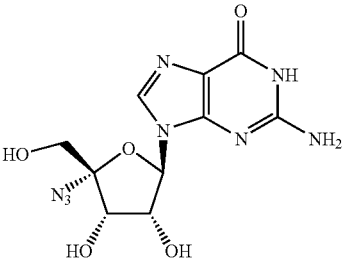 | 4'-C-Azidoguanosine |
| compound 17 | 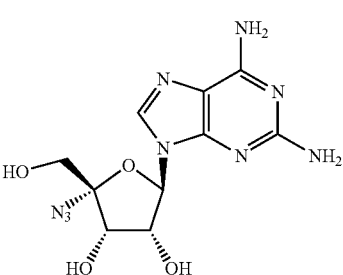 | 2-Amino-4'-C-azidoadenosine |
| compound 18 | 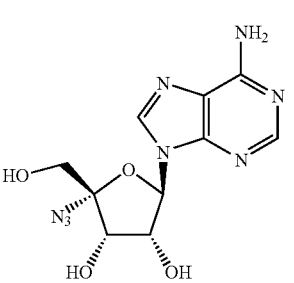 | 4'-C-Azidoadenosine |
| compound 19 | 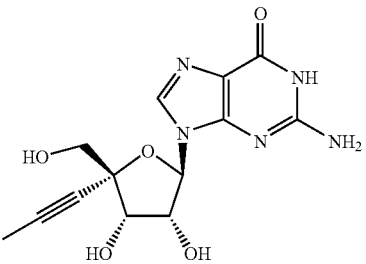 | 4'-C-(1-Propynyl)guanosine |
| compound 20 | 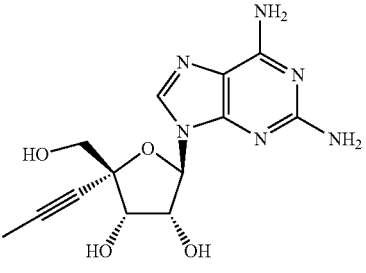 | 2-Amino-4'-C-(1-propynyl)-adenosine |

| Compound no. | STRUCTURE | Name |
|---|---|---|
| compound 21 | 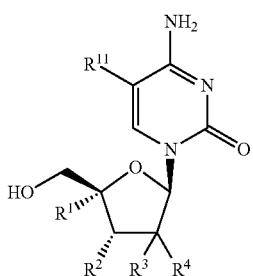 | 4'-C-(1-Propynyl)adenosine |

An especially preferred group of compounds for the treatment of HCV are those of formula I-b I-b wherein
R¹ is alkyl, alkenyl, alkynyl, haloalkyl, alkylcarbonyl, alkoxy, hydroxymethyl, cyano, azido, alkoxyiminomethyl, alkylcarbonylamino, alkylaminomethyl or dialkylaminomethyl;

R² is hydrogen, hydroxy, alkoxy, or halogen;

R³ and R⁴ are hydrogen, hydroxy, alkoxy, halogen or hydroxyalkyl, provided that at least one of R³ and R⁴ is hydrogen; or R³ and R⁴ represent fluorine.

and pharmaceutically acceptable salts.

Examples of such especially preferred compounds are listed below

| Compound no. | Structure | Name |
|---|---|---|
| compound 9 | 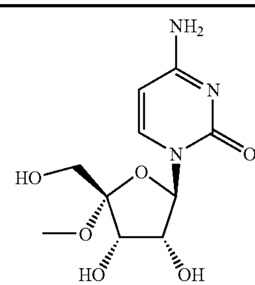 | 4'-C-Methoxycytidine |
| compound 22 | 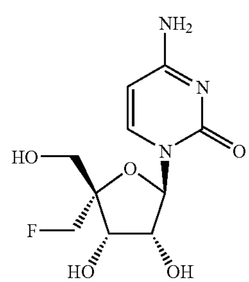 | 4'-C-(Fluoromethyl)cytidine |
| compound 23 | 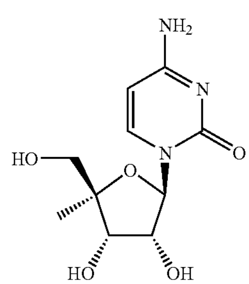 | 4'-C-Methylcytidine |

-continued

| Compound no. | Structure | Name |
|---|---|---|
| compound 24 | 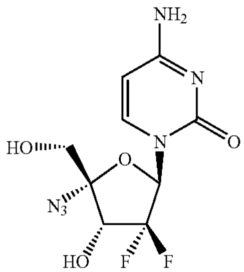 | 4'-C-Azido-2'-deoxy-2',2'-difluorocytidine |
| compound 25 | 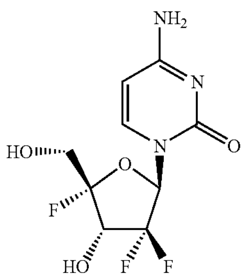 | 2'-Deoxy-4'-C-fluoro-2',2'-difluorocytidine |
| compound 26 | 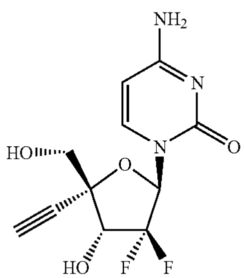 | 2'-Deoxy-4'-C-ethynyl-2',2'-difluorocytidine |
| compound 27 | 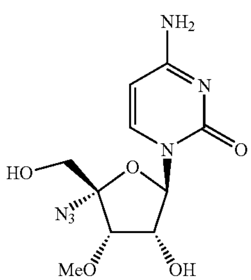 | 4'C-Azido-3'-O-methylcytidine |
| compound 28 | 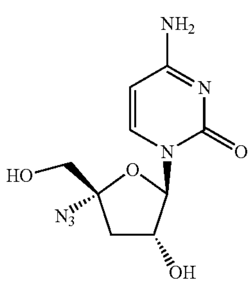 | 4'-C-Azido-3'-deoxycytidine |

-continued

| Compound no. | Structure | Name |
|---|---|---|
| compound 29 | 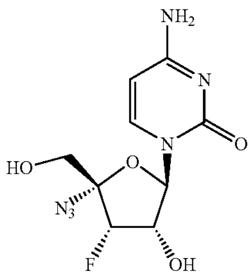 | 4'-C-Azido-3'-deoxy-3'-fluorocytidine |
| compound 30 | 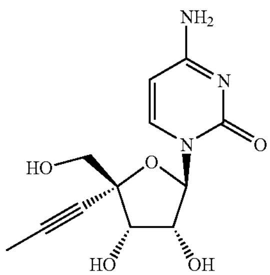 | 4'-C-(1-Propynyl)cytidine |
| compound 31 | 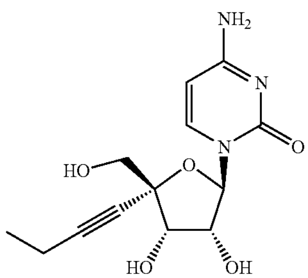 | 4'-C-(1-Butynyl)cytidine |

| Compound no. | Structure | Name |
|---|---|---|
| compound 32 | 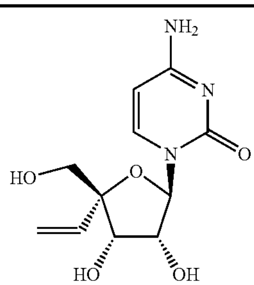 | 4'-C-Vinylcytidine |
| compound 33 | 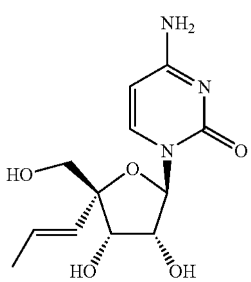 | (E)-4'-C-(1-Propenyl)cytidine |

-continued

| Compound no. | Structure | Name |
| --- | --- | --- |
| compound 34 | 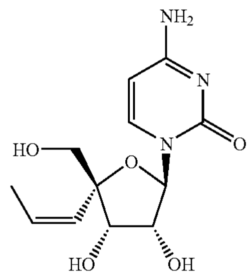 | (Z)-4'-C-(1-Propenyl)cytidine |
| compound 35 | 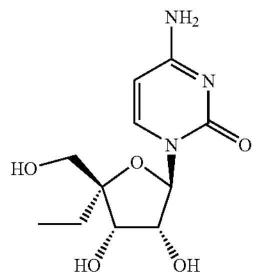 | 4'-C-Ethylcytidine |
| compound 36 | 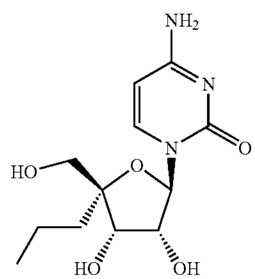 | 4'-C-Propylcytidine |
| compound 37 | 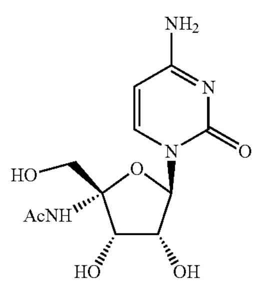 | 4'-C-Acetamidocytidine |
| compound 38 | 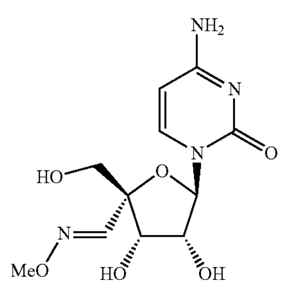 | (E)-4'-C-(Methoxyimino)cytidine |

-continued

| Compound no. | Structure | Name |
|---|---|---|
| compound 39 | 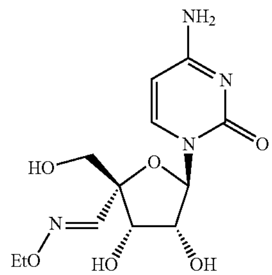 | (E)-4'-C-(Ethoxyimino)cytidine |
| compound 40 | 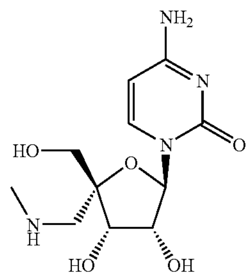 | 4'-C-[(Methylamino)methyl]-cytidine |
| compound 41 | 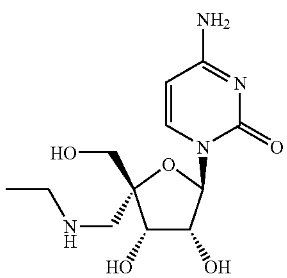 | 4'-C-[(Ethylamino)methyl]cytidine |
| compound 42 | 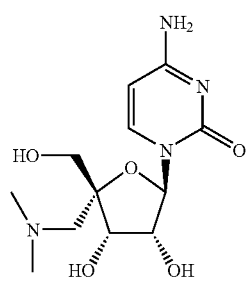 | 4'-C-[(Dimethylamino)methyl]-cytidine |
| compound 43 | 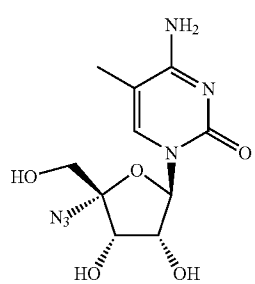 | 4'-C-Azido-5-methylcytidine |

-continued

| Compound no. | Structure | Name |
|---|---|---|
| compound 44 | 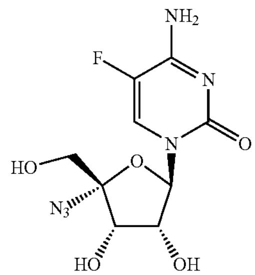 | 4'-C-Azido-5-fluorocytidine |
| compound 45 | 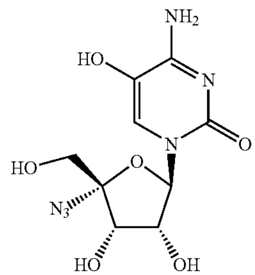 | 4'-C-Azido-5-hydroxycytidine |

Most preferred compounds for the treatment of HCV are listed below:

| Compound no. | Structure | Name |
|---|---|---|
| compound 1 (Example 1) | 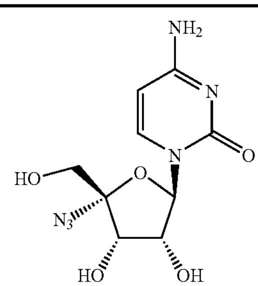 | 4'-C-Azidocytidine |
| compound 2 (Example 2) | 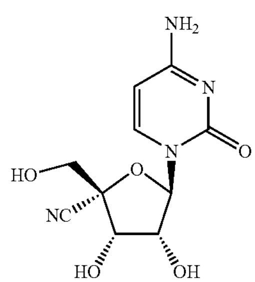 | 4'-C-Cyanocytidine |
| compound 3 (Example 3) | 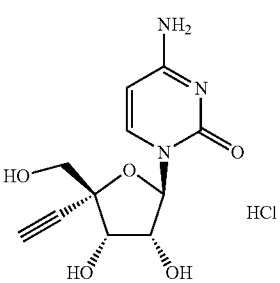 | 4'-C-Ethynylcytidine hydrochloride (1:1) |

-continued

| Compound no. | Structure | Name |
|---|---|---|
| compound 4 | 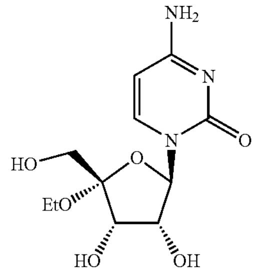 | 4'-C-Ethoxycytidine |
| compound 5 | 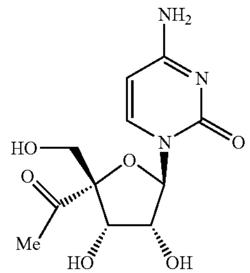 | 4'-C-Acetylcytidine |

The compounds of formula I may be prepared by various methods known in the art of organic chemistry in general and nucleoside analogue synthesis in particular. The starting materials for the syntheses are either readily available from commercial sources or are known or may themselves be prepared by techniques known in the art. General reviews of the preparation of nucleoside analogues are included in the following publications:

A M Michelson "The Chemistry of Nucleosides and Nucleotides", Academic Press, New York 1963.

L Goodman "Basic Principles in Nucleic Acid Chemistry" Ed P O P Ts'O, Academic Press, New York 1974, Vol. 1, chapter 2.

"Synthetic Procedures in Nucleic acid Chemistry" Ed W W Zorbach and R S Tipson, Wiley, New York, 1973, Vol. 1 and 2.

The synthesis of carbocylic nucleosides has been reviewed by L Agrofoglio et al, Tetrahedron, 1994, 50, 10611.

The strategies available for the synthesis of compounds of formula I include:

1. modification or interconversion of performed nucleosides; or
2. construction of the heterocyclic base after glycosylation; or
3. condensation of a protected furanose, thiofuranose or cyclopentane derivative with a pyrimidine (B2) or purine (B1) base.

These methods will be further discussed below:

1. Modification or inter-conversion of preformed nucleosides.

Such methods include on the one hand modification of the 9-purinyl or 1-pyrimidyl residue or on the other hand modification of the carbohydrate moiety.

A. Modification of the purinyl or pyrimidyl moiety:

a) The deamination of aminopurine or aminopyrimidine nucleosides as described by J. R. Tittensor and R. T. Walker European Polymer J., 1968, 4, 39 and H. Hayatsu, Progress in Nucleic Acid Research and Molecular Biology 1976, Vol. 16, p 75.

b) The conversion of the 4-hydroxy group of 4-hydroxy-pyrimidine nucleosides to a leaving group and displacement with nucleophilic reagents. Such leaving groups include halogen as described by J. Brokes and J. Beranek, Col. Czech. Chem. Comm., 1974, 39, 3100 or 1,2,4-triazole as described by K. J. Divakar and C. B. Reece, J. Chem. Soc. Perkin Trans. I, 1982, 1171.

c) 5-Substitution of pyrimidine nucleosides has been achieved by the use of 5-metallo derivatives such as 5-mercury or 5-palladium for example as described by D. E. Bergstrom and J. L. Ruth J. Amer. Chem. Soc., 1976, 98, 1587. Introduction of fluoro into the 5 position of pyrimidine nucleosides can be achieved with reagents such as trifluoromethyl hypofluorite as described by M. J. Robins, Ann New York Acad. Sci. 1975, 255, 104.

d) Modified purine nucleosides may be prepared from the corresponding purine nucleoside derivatives wherein the 2, 6 or 8 substituent is a suitable leaving group such as halogen or sulphonate or 1,3,4-triazole. 6 substituted purine nucleosides may be prepared by treatment of the appropriate 6-halopurine or 6-(1,2,4-triazol-4-yl)-purine nucleoside derivatives with the appropriate nucleophilic reagent as described by V. Nair and A. J. Fassbender Tetrahedron, 1993, 49, 2169 and by V. Samano, R. W. Miles and M. J. Robins, J. Am. Chem. Soc., 1994, 116, 9331. Similarly 8-substituted purine nucleosides can be prepared by treatment of the corresponding 8-halopurine nucleoside with the appropriate nucleophilic reagent as described by L. Tai-Shun, C. Jia-Chong, I. Kimiko and A. C. Sartorelli, J. Med. Chem., 1985, 28, 1481; Nandanan et al, J. Med. Chem., 1999, 42, 1625; J. Jansons, Y. Maurinsh, and M. Lidaks, Nucleosides Nucleotides, 1995, 14, 1709. Introduction of an 8-cyano substituent can be accomplished by displacement using a metal cyanide as described by L-L. Gundersen, Acta. Chem. Scand. 1996, 50, 58. 2-Modified purine nucleoside may be prepared in a similar fashion as described by T. Steinbrecher, C. Wamelung, F. Oesch and A. Seidl, Angew. Chem. Int. Ed. Engl., 1993, 32, 404.

e) Where the substituent at the 2 or 8-position of the purine nucleoside is linked via a carbon carbon bond e. g. alkyl, then metal catalysed cross-coupling procedures can be used starting with the appropriate 2 or 8-halosubstituted purine nucleoside analogue as described by A. A. Van Aerschott, et al, J.

Med. Chem., 1993, 36, 2938; V. Nair and G. S. Buenger, J. Am. Chem. Soc., 1989, 111(22), 8502; C. Tu, C. Keane and B. E. Eaton Nucleosides Nucleotides, 1995, 14, 1631.

B. Modification of the carbohydrate moiety:

Following introduction of protecting groups which are compatible with the further chemistry:

Azide may be introduced at the 4'-position by treatment of the 4',5'-didehydro nucleoside with iodine azide as exemplified by H. Maag et al, J. Med. Chem., 1992, 35, 1440. An alkoxide may be introduced at the 4'-position by treatment of the 4',5'-didehydro nucleoside with iodine followed by an alcohol and lead carbonate as exemplified by J. P. Verheyden and J. G. Moffatt, J. Am. Chem. Soc., 1975, 97(15), 4386. Fluoride may be introduced at the 4'-position by treatment of the 4',5'-didehydro nucleoside with iodine followed by silver(I)fluoride as described by G. R. Owen et al, J. Org. Chem., 1976, 41(8), 3010 or A. Maguire et al, J. Chem. Soc. Perkin Trans. 1, 1993, 1(15), 1795. A 4'-formyl group can be introduced and subsequently converted to a wide range of substituents including but not limited to 4'-haloalkyl, 4'-ethynyl, 4'-oximinomethyl, and 4'-cyano as exemplified by M. Nomura et al., J. Med. Chem., 1999, 42, 2901.

Modification of either the 2'-hydroxy substituent or 3'-hydroxy substituent in the nucleoside analogue is possible.

Conversion of the 3-hydroxy to a leaving group such as halo by reaction with for example triphenyl phosphine and a tetrahaloalkane as described for example by L. De Napoli et al, Nucleosides Nucleotides, 1993, 12, 981, followed by reduction provides the 3-deoxysugar derivatives as described by D. G. Norman and C. B. Reese, Synthesis 1983, 304.

Derivatisation of the 3 hydroxy group by conversion to a triflate group followed by reduction using sodium borohydride as described by S. A. Surzhykov et al, Nucleosides Nucleotides, 1994, 13(10), 2283. Direct introduction of a fluorine substituent can be accomplished with fluorinating agents such as diethylaminosulphur trifluoride as described by P. Herdewijn, A. Van Aerschot and L. Kerremans, Nucleosides Nucleotides, 1989, 8, 65.

Conversion of the hydroxy substituent to a leaving group such as halo or sulphonate also allows displacement using nucleophilic reagents such as tetrabutylammonium fluoride, lithium azide, or metal cyanides as exemplified by H. Hrebabecky, A. Holy and E. de Clercq, Collect. Czech. Chem. Comm. 1990, 55, 1800; K. E. B. Parkes and K. Taylor, Tet. Lett., 1988, 29, 2995; H. M. Pfundheller et al, Helv. Chim. Acta, 2000, 83, 128.

Reaction of 2'-keto nucleosides with fluorinating agents such as diethylamino sulfur trifluoride can be used to prepare 2',2'-difluoronucleosides as described by D. Bergstrom, E. Romo and P. Shum Nucleosides Nucleotides, 1987, 6, 53.

2. Construction of the heterocyclic base after glycosylation.

a) those which for example utilise furanosylamine derivatives as described by N. J. Cusack, B. J. Hildick, D. H. Robinson, P. W. Rugg and G. Shaw J. Chem. Soc. Perkin Trans., I 1973, 1720 or G. Shaw, R. N. Warrener, M. H. Maguire and R. K. Ralph, J. Chem. Soc., 1958, 2294.

b) those which utilise for example furanosylureas for pyrimidine nucleoside synthesis as described by J. Šmejkal, J. Farkas, and F. Šorm, Coll. Czech. Chem. Comm., 1966, 31, 291.

c) the preparation of purine nucleosides from imidazole nucleosides is reviewed by L. B. Townsend, Chem. Rev., 1967, 67, 533.

d) the preparation of compounds of formula I wherein X is $CH_2$ can be accomplished from 1-hydroxymethyl-4-aminocyclopentane derivatives as described by Y. F. Shealy and J. D. Clayton J. Am. Chem. Soc., 1969, 91, 3075; R. Vince and S. Daluge J. Org. Chem., 1980, 45, 531; R. C. Cermak and R. Vince, Tet. Lett., 1981, 2331; R. D. Elliott et al, J. Med. Chem., 1994, 37, 739.

3. Condensation of a protected furanose, thiofuranose or cyclopentane derivative with a purine or pyrimidine derivative.

The condensation reaction of a protected furanose, thiofuranose or cyclopentane derivative with an appropriate purine or pyrimidine derivative may be performed using standard methods including the use of a Lewis acid catalyst such as mercuric bromide or stannic chloride or trimethylsilyltrifluoromethane sulphonate in solvents such as acetonitrile, 1,2-dichloroethane, dichloromethane, chloroform or toluene at reduced, ambient or elevated temperature. Examples for the condensation reaction of a protected furanose or thiofuranose with heavy metal derivatives of purines or pyrimidines derivatives (e. g. chloromercury derivatives) are described by J Davoll and B. A. Lowry, J. Am. Chem. Soc., 1951, 73, 1650; J. J. Fox, N. Yung, J. Davoll and G. B. Brown, J. Am. Chem. Soc., 1956, 78, 2117.

with alkoxy pyrimidines are described by K. A. Watanabe, D. H. Hollenberg and J. J. Fox., Carbohydrates. Nucleosides and Nucleotides. 1974, 1, 1.

with silyl derivatives of purines or pyrimidines as described by U. Niedballa and H. Vorbruggen, J. Org. Chem., 1976, 41, 2084; U. Niedballa and H. Vorbruggen, J. Org. Chem., 1974, 39, 3672. A. J. Hubbard, A. S. Jones and R. T. Walker, Nucleic Acids Res., 1984, 12, 6827.

Furthermore the fusion of per-acylated sugars with purines under vacuum in the presence of p-toluene sulphonic acid has been described by T. Simadate, Y. Ishudo and T. Sato, Chem. Abs., 1962, 56, 11 692 and W. Pfleiderer, R. K. Robins, Chem. Ber. 1965, 98, 1511.

the condensation reactions have been described by K. A. Watanabe, D. H. Hollenberg and J. J. Fox, Carbohydrates Nucleosides and Nucleotides, 1974, 1, 1.

Examples for the condensation reaction of a protected cyclopentane derivative with an appropriate purine derivative or pyrimidine derivative are given in H. Kapeller, H. Baumgartner and H. Griengl, Monattsh Chem., 1997, 128, 191 and P. Wang et al, Tet. Lett., 1997, 38, 4207; or by T. Jenny et al. Helv. Chim. Acta, 1992, 25, 1944.

Such methods often result in mixtures of anomeric nucleoside derivatives which can be separated by standard techniques known to the art such as recrystallisation, column chromatography, high performance liquid chromatography or super critical fluid chromatography.

The purine derivatives and pyrimidines derivatives for above condensation reactions can be obtained commercially or can be prepared by procedures known to the art.

The preparation of purine derivatives is reviewed by G. Shaw in "Comprehensive Heterocyclic Chemistry" pub Pergamon Press Vol. 5 chapter 4. 09, p 499 and "Comprehensive Heterocyclic Chemistry II" publ. Pergamon Press, Vol 7, chapter 7. 11, p 397

The preparation of pyrimidines derivatives is reviewed by D. J. Brown in "The Chemistry of Heterocyclic Compounds—The Pyrimidines" 1962 and Supplement 1, 1970, pub John Wiley and Sons, New York, by D. J. Brown in "Comprehensive Heterocyclic Chemistry" pub Pergamon Press Vol. 5 chapter 4. 09, p 499 and by K. Unheim and T.

Benneche in "Comprehensive Heterocyclic Chemistry II" pub Pergamon Press Vol. 6 chapter 6. 02 p 93

Furanose derivatives can be prepared from commercially available carbohydrate starting materials such as the D forms of ribose, arabinose, xylose or lyxose, following introduction of protecting groups which are compatible with the chemistry.

4-Substituted furanoses with the substituent containing a carbon attached to the 4-position of the furanose, for example alkyl, alkenyl, alkynyl, haloalkyl, acyl, alkoxycarbonyl, hydroxyalkyl, alkoxyalkyl, cyano, oximinomethyl, alkoxyiminomethyl, alkylaminocarbonyl and acyl can be prepared from the corresponding 4-formyl furanose. The preparation of one such 4-formylfuranose is described by H. Ohrui et al., J. Med. Chem., 2000, 43, 5416. 4-Haloalkyl furanoses may be prepared from the corresponding 4-hydroxymethyl furanoses (e.g., K. Kitano et al, Tetrahedron, 1997, 53(39), 13315). 4-Methyl furanoses can be prepared by the method described by T. Waga et al, Biosci. Biotech. Biochem. 1993, 19(7), 408.

2,2-Difluorofuranose derivatives can be prepared from D-glucose or D-mannose as described by R. Fernandez, M. I. Mateu, R. Echarri and S. Castillon Tetrahedron, 1998, 54, 3523. The thiofuranose derivatives can be prepared by literature procedures such as L. Bellon, J. L. Barascut, J. L. Imbach, Nucleosides and Nucleotides 1992, 11, 1467 and modified in a similar fashion to the furanose analogues described above.

The cyclopentane derivatives can be prepared by methods known in the art of organic chemistry and by methods and references included in L. Agrofolio et al., Tetrahedron, 1994, 50, 10611.

The preformed nucleoside derivatives are either available commercially or synthesised in accordance with the methods described above.

The methods discussed above are described in more details below:

The compounds of formula I, wherein $R^1$ is $N_3$, $R^2$ and $R^3$ are hydroxy and B is B2 can be prepared according to Reaction Scheme A:

Scheme A

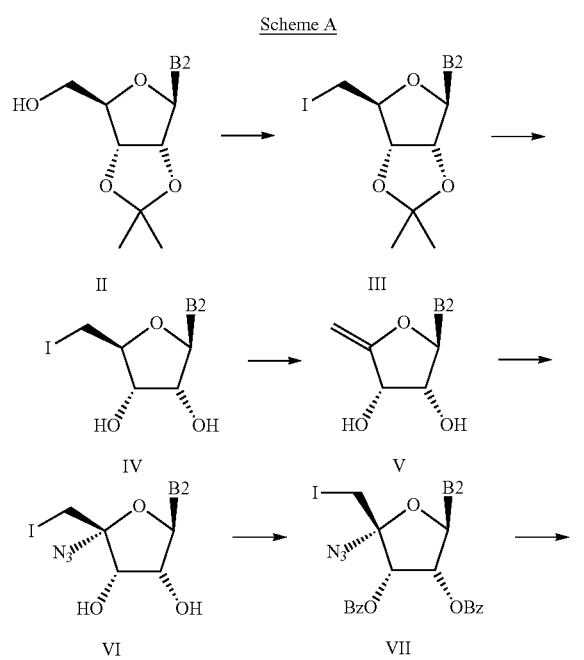

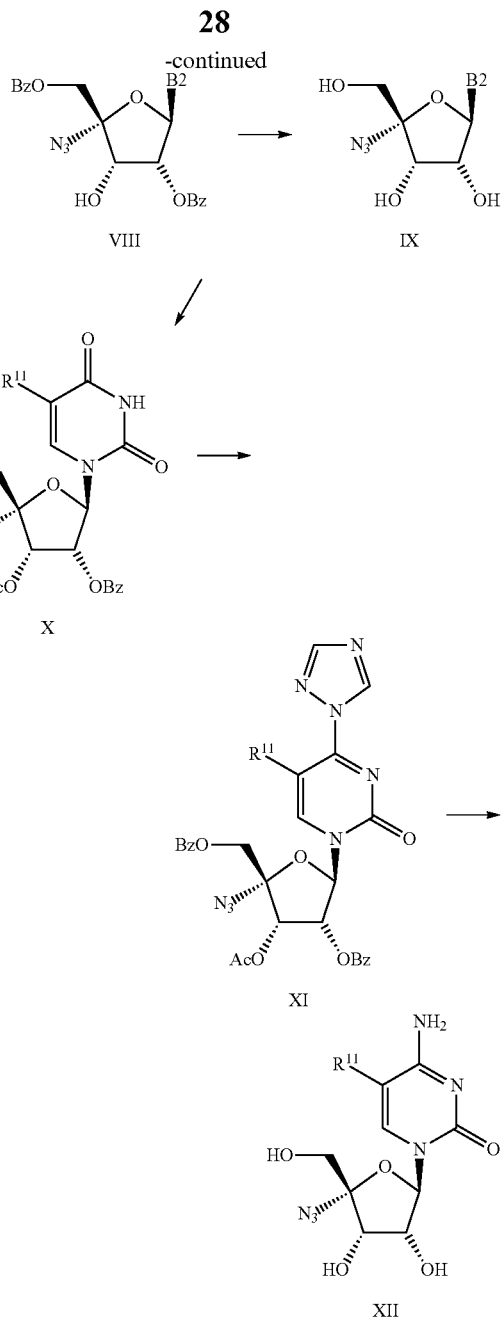

wherein Ac is acetyl, Bz is benzoyl and $R^{11}$ is as defined above.

Compounds of Formula II may be iodinated using a mixture of triphenylphosphine, iodine and pyridine as exemplified by H. Maag et al, J. Med. Chem., 1992, 35, 1440. The acetonide protecting group can be removed by treatment with an acid, for instance acetic acid, as described by J. P. Verheyden et al, J. Org. Chem., 1970, 35(7), 2319, to give nucleosides of formula III. Following protection of the 2' and 3' hydroxyls with acetic anhydride and pyridine elimination of hydrogen iodide, with for example silver fluoride in pyridine and removal of the acetyl protecting groups with methanolic ammonia as described by J. P. Verheyden et al., J. Org. Chem., 1974, 39(24), 3573, gives 4',5' didehydro nucleosides of formula V. Addition of iodine azide to the double bond can be accomplished by treatment of V with a mixture of iodine chloride and sodium azide in N,N-dimethylformamide as described by H. Maag et al, J. Med. Chem., 1992, 35, 1440, to give nucleosides of formula VI. Protection of the hydroxy groups in VI can be accomplished by treatment of VI with benzoyl chloride in pyridine, giving nucleosides of formula VII, which can then be converted into the 5'-benzoyl nucleosides of formula VIII by treatment with meta-chloroperbenzoic acid in dichloromethane, which can then be deprotected with a base, eg sodium methoxide, in methanol to give nucleosides of formula IX, all as described by H. Maag et al, J. Med. Chem., 1992, 35, 1440. In the case where B2 in the compound of formula VIII is uracil or 5'-substituted uracil, following protection of the 3'-hydroxy group with acetic anhydride and pyridine, conversion to the corresponding cytidine of formula XII can be accomplished by the method described by A. D. Borthwick et al., J. Med. Chem., 1990, 33 (1), 179, whereby nucleosides of formula X can be treated with 4-chlorophenyl dichlorophosphate and triazole to give 4-triazolyl nucleosides of formula XI, followed by treatment of nucleosides XI with aqueous ammonia giving 5-substituted cytidines of formula XII.

Compounds of formula I, wherein $R^1$ is —C≡CH, —CH=CHCl, —CH=N—OH, —CN, $R^2$ and $R^3$ are hydroxy and B is B1 or B2 can be prepared according to Reaction Scheme B.

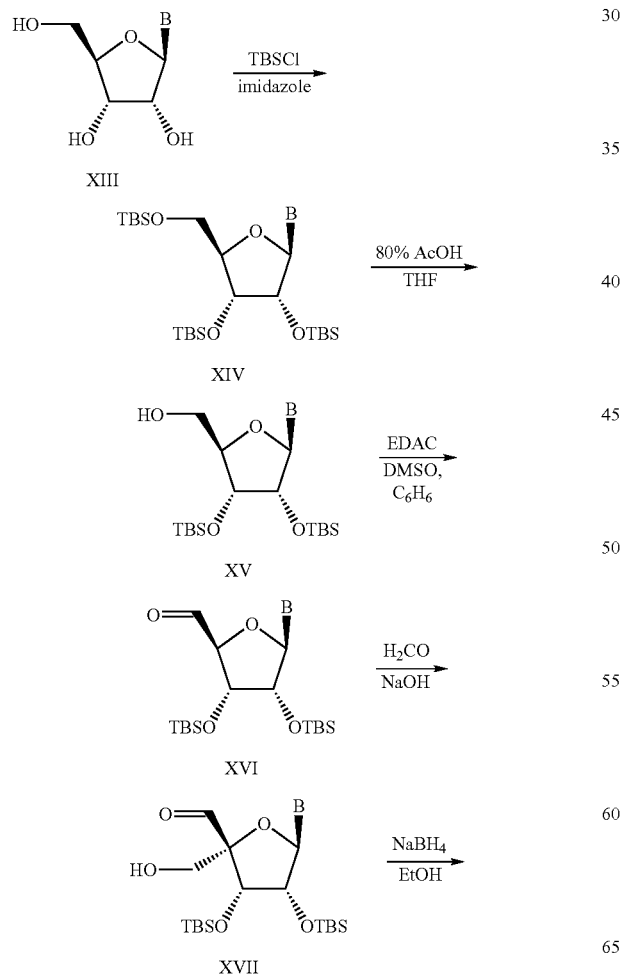
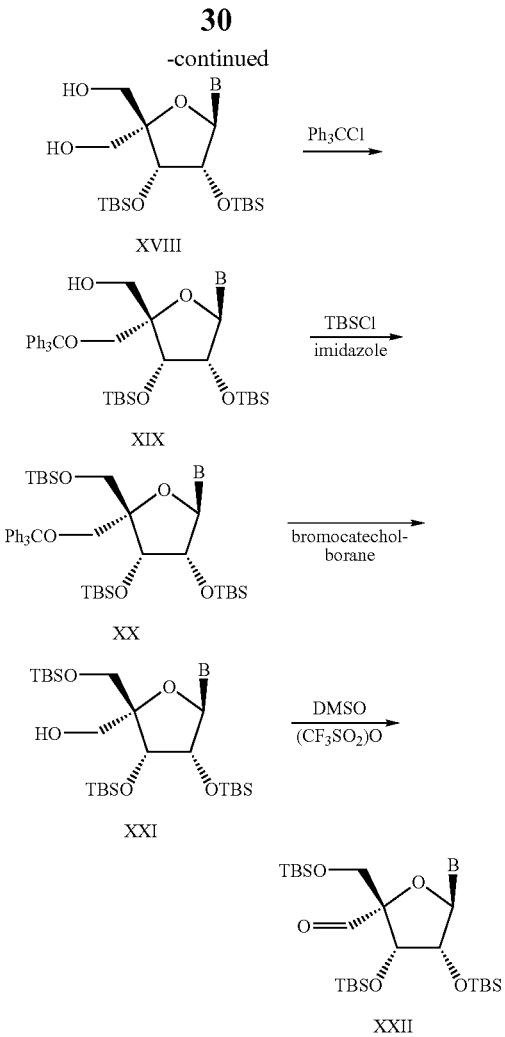

Compounds of formula XIII can be silylated with tert-butyldimethylsilylchloride (TBSCl) and imidazole to give the tri-tert-butyldimethylsilyl compounds of formula XIV. The 5'-tert-butyldimethylsilyl ether can be deprotected using 80% acetic acid to give the 5-hydroxy nucleosides XV, which can then be oxidised to the 5'-formyl nucleosides XVI using a mixture of 1-(3-dimethyl-aminopropyl)-3-ethylcarbodiimide hydrochloride (EDAC) and dimethylsulphoxide (DMSO) in a suitable solvent, eg benzene. Alkylation of XVI with formaldehyde and sodium hydroxide gives the 4'-hydroxymethyl compounds XVII which can be reduced to the 4'-dihydroxymethyl compounds XVIII. Selective protection of the hydroxymethyl on the α face of the nucleoside with trityl chloride in pyridine gives the 4'-trityl compounds XIX, followed by protection of the hydroxymethyl on the β-face of the nucleoside with tert-butyldimethylsilylchloride (TBSCl) and imidazole gives compounds of formula XX. Deprotection of the trityl group with bromocatecholborane gives the 4'-hydroxymethyl compound XXI, which can be oxidised with trifluoromethanesulphonic anhydride and dimethylsulphoxide to give the 4'-formyl compound of formula XXII.

The aldehyde of formula XXII can be used as starting material for a wide range of 4'-substituted nucleosides as depicted in Scheme C:

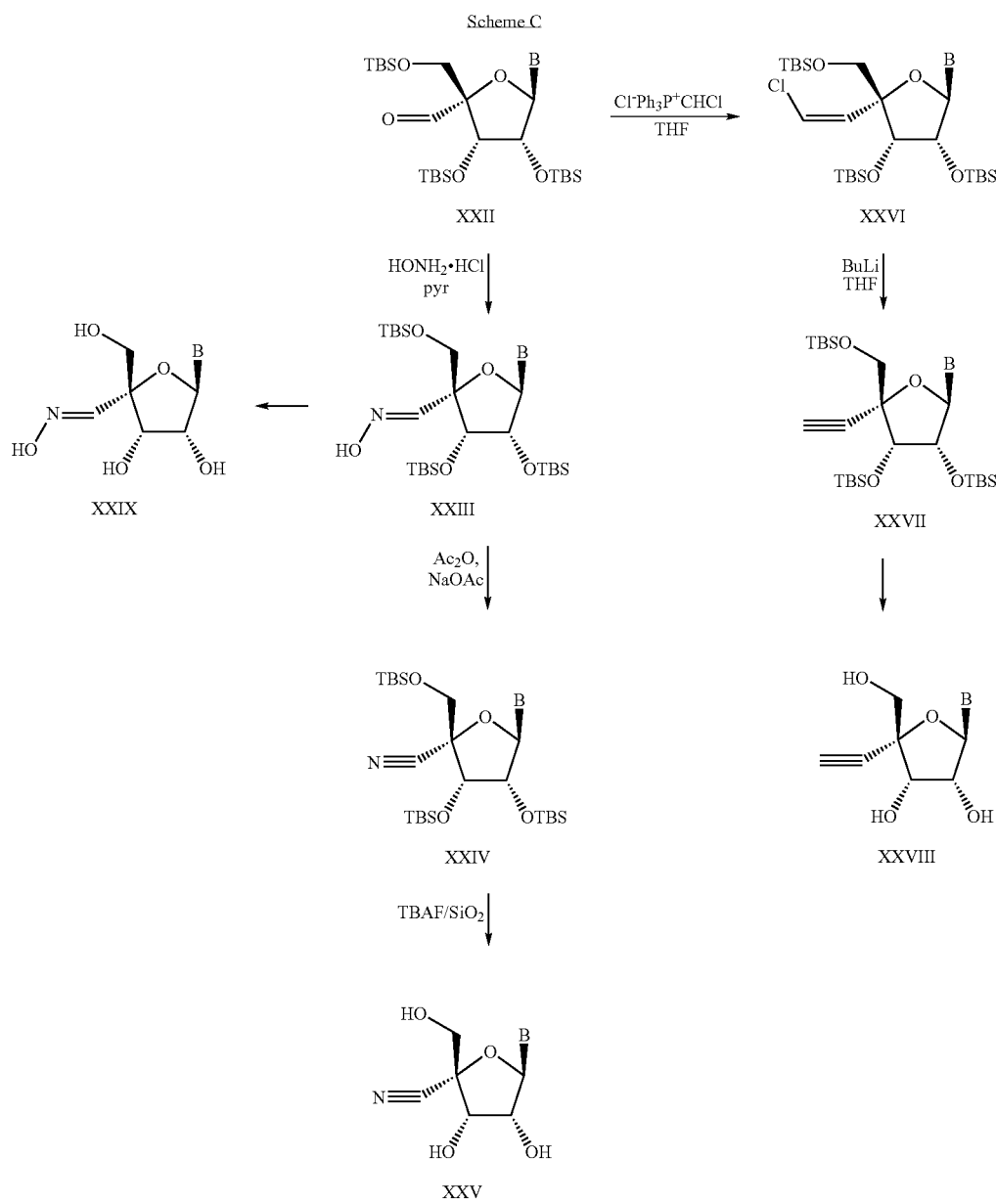

Scheme C

Treatment of the aldehyde XXII with hydroxylamine hydrochloride and pyridine gives the 4'-hydroxyimine of formula XXIII. Water is eliminated from compound XXIII to give 4'-cyano compounds of formula XXIV. Treatment of 4'-formyl compounds of formula XXII with chloromethyl-phosphonium chloride and butyl lithium gives the 4'-(2-chloroethenyl) compounds XXVI. Treatment of compounds XXVI with butyllithium results in the elimination of hydrogen chloride to give the 4'-ethynyl compounds of formula XXVII. Removal of the silyl protecting groups from the tri tert-butyldimethylsilylchloride protected compounds XXIII, XXVII and XXIV can be carried out with a fluoride source such as ammonium fluoride in methanol or tetrabutylammonium fluoride absorbed on silica in tetrahydrofuran, to give the respective 4'-substituted nucleosides XXV, XXVIII and XXIX.

Suitably protected 4'-substituted uridines (for example XXIV and XXVII) can be converted to the corresponding 4'-substituted cytidines according to Reaction Scheme D.

Scheme D

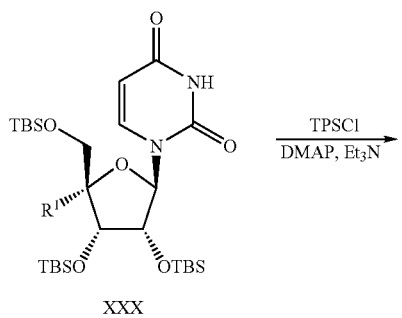

XXX

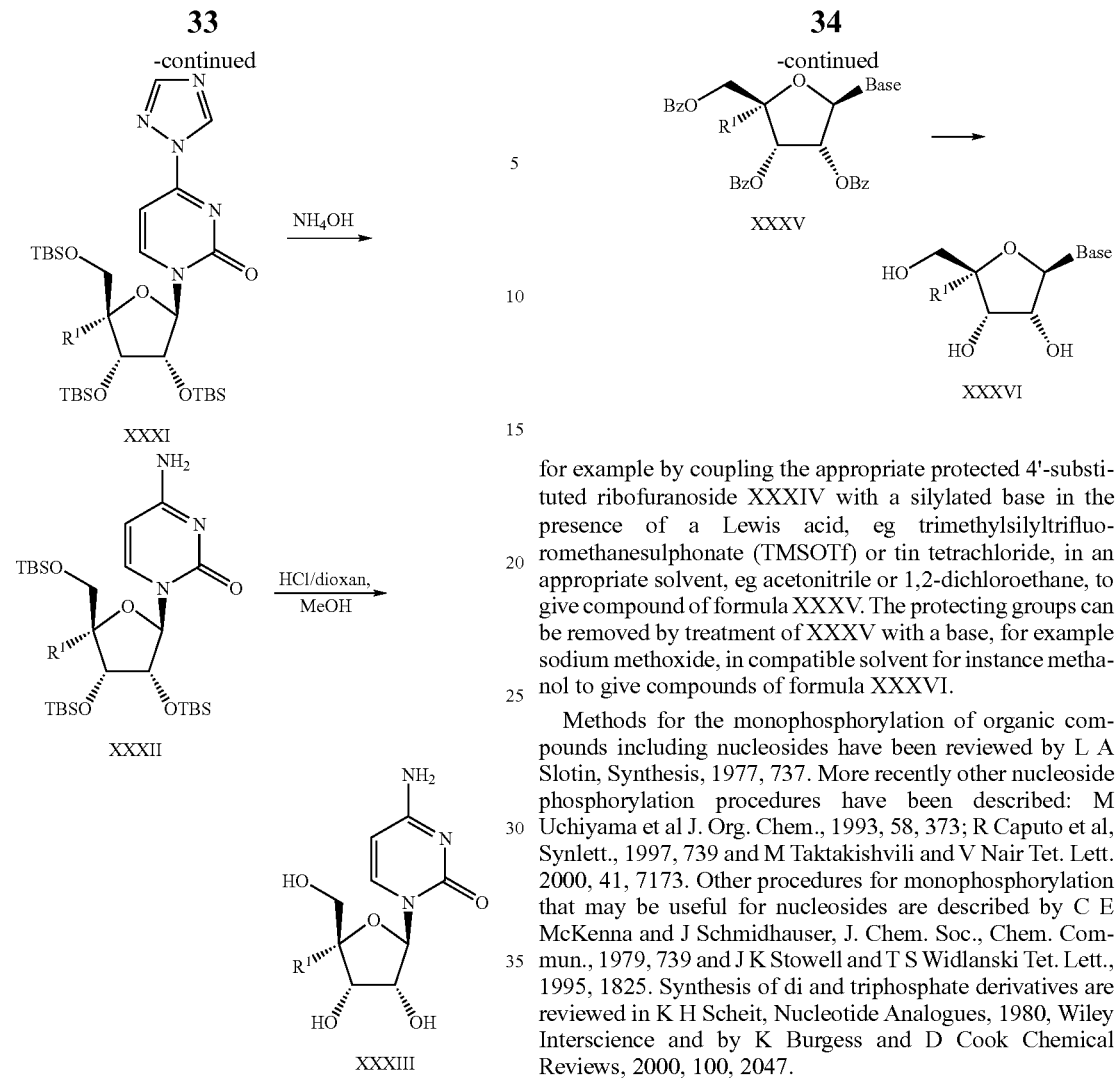

The tri-tertbutyldimethylsilyl (TBS) protected uridines of formula XXX can be treated with tri-isopropylbenzenesulphonyl chloride, triethylamine and dimethylaminopyridine to give the 4-triazolylnucleosides XXXI. The 4-triazolyl compounds XXXI can be converted to the 4-amino compounds XXXII with aqueous ammonia. Deprotection of the silyl groups with a mixture of methanol and hydrochloric acid in dioxan gives the cytidine derivatives XXXIII.

Compounds of formula I, wherein $R^1$ is alkoxy, $R^2$ and $R^3$ are hydroxy and B is a 9-purinyl residue B1 or a 1-pyrimidyl residue B2 can be prepared according to the procedures described by J. P. Verheyden et al. U.S. Pat. No. 3,910,885

Compounds of formula I in which $R^1$ is trifluoromethyl, methyl or ethynyl can be prepared as depicted in Reaction Scheme E:

Scheme E

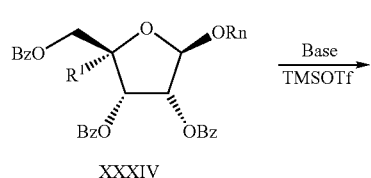

XXXIV for example by coupling the appropriate protected 4'-substituted ribofuranoside XXXIV with a silylated base in the presence of a Lewis acid, eg trimethylsilyltrifluoromethanesulphonate (TMSOTf) or tin tetrachloride, in an appropriate solvent, eg acetonitrile or 1,2-dichloroethane, to give compound of formula XXXV. The protecting groups can be removed by treatment of XXXV with a base, for example sodium methoxide, in compatible solvent for instance methanol to give compounds of formula XXXVI.

Methods for the monophosphorylation of organic compounds including nucleosides have been reviewed by L A Slotin, Synthesis, 1977, 737. More recently other nucleoside phosphorylation procedures have been described: M Uchiyama et al J. Org. Chem., 1993, 58, 373; R Caputo et al, Synlett., 1997, 739 and M Taktakishvili and V Nair Tet. Lett. 2000, 41, 7173. Other procedures for monophosphorylation that may be useful for nucleosides are described by C E McKenna and J Schmidhauser, J. Chem. Soc., Chem. Commun., 1979, 739 and J K Stowell and T S Widlanski Tet. Lett., 1995, 1825. Synthesis of di and triphosphate derivatives are reviewed in K H Scheit, Nucleotide Analogues, 1980, Wiley Interscience and by K Burgess and D Cook Chemical Reviews, 2000, 100, 2047.

The following Examples illustrate methods for the preparation of compounds of formula I:

EXAMPLE 1

Preparation of Compound 1, According to the Method of Schemes 1 and 1a

Scheme 1

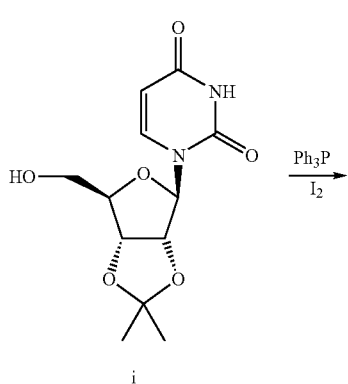

i

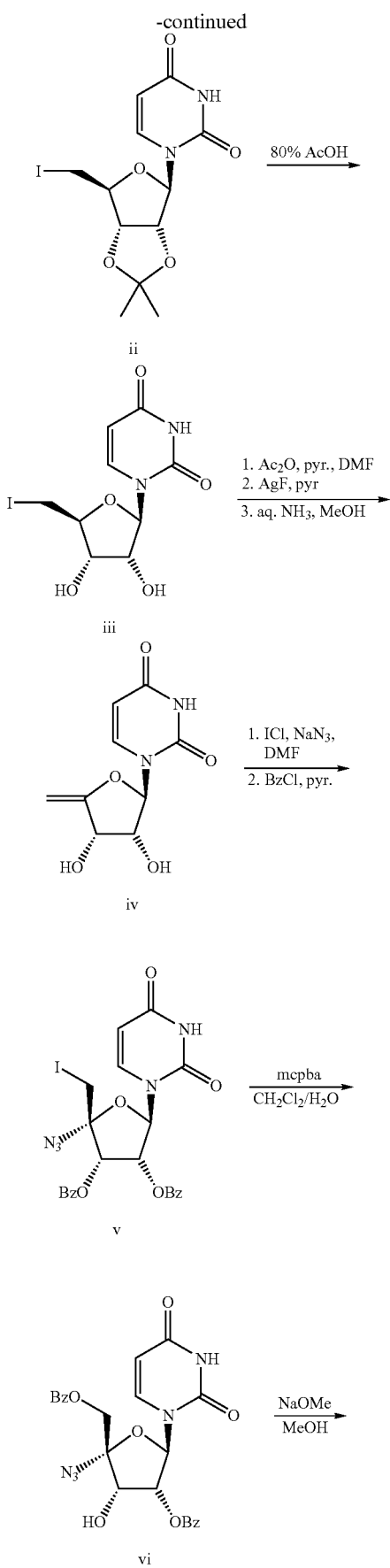

1.1. Compound (i)

Compound (i) was purchased from Lancaster (Cat. no.: 206-647-7, CAS 362-43-6)

1.2. Compound (ii)

Triphenylphosphine (1.57 g, 6.0 mmol) and iodine (1.52 g, 6.0 mmol) were added to compound (i) (1.14 g, 4.0 mmol) in dioxan (20 ml) containing pyridine (0.65 mmol, 8.0 mmol). The mixture was stirred overnight and quenched with methanol (1 ml). The solvent was evaporated in vacuo. The residue was dissolved in ethyl acetate (200 ml), washed with water (100 ml), 10% aqueous sodium thiosulphate (100 ml), brine (100 ml) and dried over anhydrous magnesium sulphate. The magnesium sulphate was removed by filtration and the filtrate evaporated in vacuo. The residue was purified by flash column chromatography on silica gel, eluting with 1:1 ethyl acetate/petrol) to afford compound (ii) as a colourless oil which slowly solidified to a colourless waxy solid (1.5 g) mass spectrum (CI) m/z 395 $[M+H]^+$.

1.3. Compound (iii)

Compound (iii) was prepared from compound (ii) as described by J. P. Verheyden et al., J. Org. Chem., 1970, 35(7), 2319.

1.4. Compound (iv)

Compound (iv) was prepared from compound (iii) as described by J. P. Verheyden et al., J. Org. Chem., 1974, 39(24), 3573.

1.5. Compound (v)

Compound (v) was prepared from compound (iv) as described by H. Maag et al., J. Med. Chem., 1992, 35, 1440-1451.

1.6. Compound (vi)

To a solution of compound (v) (482 mg, 0.80 mmol) in dichloromethane saturated with water (10 ml) was added 55% metachloroperbenzoic acid (1.0 g, 4.95 mmol). The mixture was stirred for 2 h. Additional metachloroperbenzoic acid (0.50 g) was added and the mixture was stirred for an additional 3 h. Ethyl acetate (100 ml) was added and the solution washed with 10% sodium metabisulphite solution (50 ml), followed by saturated sodium hydrogen carbonate solution (50 ml). The ethyl acetate was dried over anhydrous magnesium sulphate. The magnesium sulphate was removed by filtration and the filtrate was evaporated in vacuo. The residue was subjected to flash chromatography, eluting with 1:1 ethyl acetate/petrol 1:1 to afford compound (vi) as a colourless glass (200 mg); mass spectrum (ESI) m/z 535 $[M+H+CH_3CN]^+$ 1.7. Compound (vii)

To a solution of compound (vi) (170 mg, 0.35 mmol) in methanol (2 ml) was added a solution of sodium methoxide in methanol (0.5 M, 0.5 ml). The solution was stirred for 2 h at room temperature. The solution was neutralised with ion exchange resin (Amberlite IRC 50 ($H^+$), Aldrich, cat. no. 42, 883-3) and stirred for 10 min. The resin was removed by filtration. The filtrate was evaporated in vacuo and the residue was subjected to flash chromatography eluting with 1:1 ethyl acetate/acetone) to afford a colourless oil. Trituration with ethyl acetate afforded compound (vii) as a colourless solid (35 mg); mass spectrum (CI) m/z 286 [M+H]+.

The transformation of the azidouridine derivative to the corresponding azidocytidine derivative (compound 1) and its hydrochloride salt is depicted in Scheme 1a

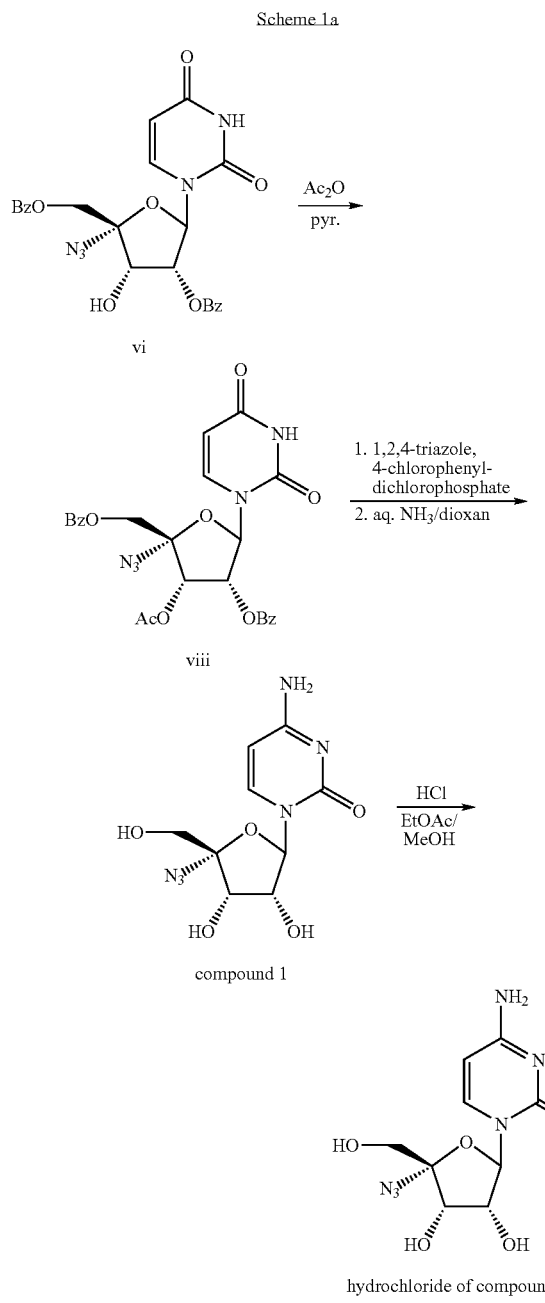

1.8. Compound (viii)

To a solution of compound (vi) (460 mg, 0.93 mmol) in pyridine (3 ml) was added acetic anhydride (1 ml) and the mixture was stirred for 4 h. Ethyl acetate (100 ml) was added and the mixture was washed with 2 N HCl (50 ml), followed by saturated sodium hydrogen carbonate solution (50 ml).

The solution was dried over anhydrous magnesium sulphate. The magnesium sulphate was removed by filtration and the filtrate was evaporated in vacuo. The residue was subjected to flash chromatography eluting with 1:1 ethyl acetate/petrol to afford compound (viii) as a colourless gum (350 mg); mass spectrum (ESI) m/z 536 [M+H]+

1.9. Compound 1

To a solution of compound (viii) (1.5 g, 2.8 mmol) in pyridine (20 ml) was added 1,2,4-triazole (0.97 g, 14 mmol). 4-chlorophenyldichlorophosphate (1.36 ml, 8.4 mmol) was then added dropwise with stirring. The mixture was stirred for 16 h. Ethyl acetate (300 ml) was added and the mixture was washed with saturated sodium hydrogen carbonate solution (200 ml). The solution was dried over anhydrous magnesium sulphate. The magnesium sulphate was removed by filtration and the filtrate was evaporated in vacuo. The residue was subjected to flash chromatography eluting with 2:1 ethyl acetate/petrol to afford a yellow foam (850 mg). The foam was treated with dioxan (8 ml) followed by aqueous ammonia solution (16 ml) and stirred for 16 h. The filtrate was evaporated in vacuo and the residue was subjected to flash chromatography eluting with 90:18:3:2 dichloromethane/methanol/acetic acid/water to afford compound 1 as a light tan foam (350 mg); mass spectrum (FAB) m/z 285 [M+H]+

1.10. Hydrochloride of Compound 1

Compound 1 (0.40 g) was dissolved in methanol and treated with a solution of hydrogen chloride in ethyl acetate. The product separated as a microcrystalline solid and was collected by filtration and dried in vacuo to afford the hydrochloride salt of compound 1 (0.22 g); mass spectrum (ESI) m/z 285 [M+H]+

EXAMPLE 2

Preparation of Compound 2 According to the Method of Scheme 2

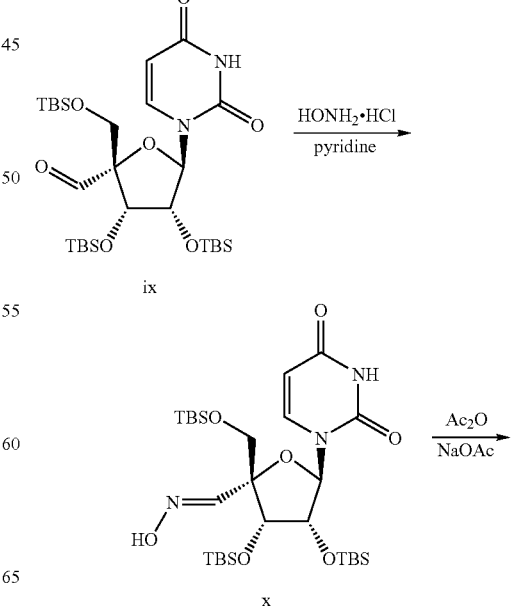

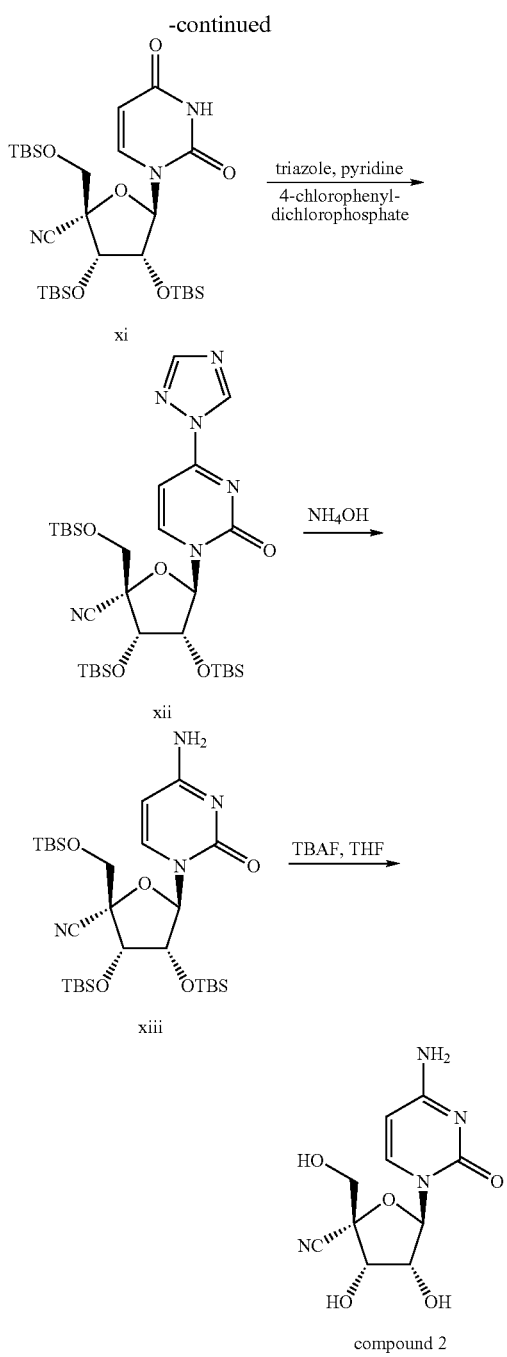

2.1. Compound (ix)

Compound (ix) was prepared from compound (xiv), see example 3, as described by M. Nomura et al., J. Med. Chem., 1999, 42, 2901-2908.

2.2. Compound (x)

A mixture of (ix) (600 mg, 0.98 mmol) and hydroxylamine hydrochloride (140 mg, 1.95 mmol) in pyridine was stirred at room temperature for 2 h. The reaction mixture was evaporated in vacuo and the residue was partitioned between ethyl acetate (30 ml) and water (30 ml). The ethyl acetate layer was separated and dried over anhydrous magnesium sulphate. The magnesium sulphate was removed by filtration and the filtrate evaporated in vacuo to afford compound (x) as a white foam (615 mg); mass spectrum (ESI) m/z 630 [M+H]$^+$.

2.3. Compound (xi)

A mixture of compound (x) (550 mg, 0.87 mmol) and sodium acetate (720 mg, 5.25 mmol) was suspended in acetic anhydride then heated at 130° C. for 3 h. The reaction mixture was evaporated in vacuo and the residue partitioned between ethyl acetate (30 ml) and saturated sodium bicarbonate (30 ml). The ethyl acetate layer was separated and dried over anhydrous magnesium sulphate. The magnesium sulphate was removed by filtration and the filtrate evaporated in vacuo. The residue was purified by flash column chromatography on silica gel, eluting with 1:2 diethyl ether/hexane. Product containing fractions were combined and evaporated in vacuo to afford compound (xi) as a colourless solid (285 mg). mass spectrum (ESI) m/z 612 [M+H]$^+$.

2.4. Compound (xii)

4-chlorophenyl-dichlorophosphate (160 μL, 0.98 mmol) was added dropwise to a solution of compound (xi) (200 mg, 0.33 mmol) and 1,2,4-triazole (115 mg, 1.63 mmol) in anhydrous pyridine (5 ml) then stirred at room temperature for 16 h. The reaction mixture was evaporated in vacuo and the residue partitioned between ethyl acetate (30 ml) and 2M hydrochloric acid (30 ml). The ethyl acetate layer was separated, washed with saturated sodium bicarbonate (30 ml) and dried over anhydrous magnesium sulphate. The magnesium sulphate was removed by filtration and the filtrate evaporated in vacuo. The residue was purified by flash column chromatography on silica gel, eluting with 1:1 diethyl ether/hexane followed by 2:1 diethyl ether/hexane. Product containing fractions were combined and evaporated in vacuo to afford (xii) as a cream solid (65 mg). mass spectrum (ESI) m/z 663 [M+H]$^+$.

2.5. Compound (xiii)

A solution of compound (xii) (60 mg, 0.09 mmol) and aqueous ammonia (2 ml) in acetonitrile was stirred at room temperature for 16 h. The reaction mixture was evaporated in vacuo and the residue partitioned between ethyl acetate (10 ml) and 2 M hydrochloric acid (10 ml). The ethyl acetate layer was separated and dried over magnesium sulphate. The magnesium sulphate was removed by filtration and evaporated in vacuo to afford compound (xiii) as a pale yellow solid (45 mg); mass spectrum (ESI) m/z 611 [M+H]$^+$

2.6. Compound 2

Tetrabutylammonium fluoride (1 M solution in THF, 0.3 ml) was added to a stirred solution of compound (xiii) (40 mg, 0.06 mmol) in dry tetrahydrofuran (10 ml) and stirred at room temperature for 2 h. The solvent was removed by evaporation in vacuo The residue was treated with pyridine (1 ml) followed by acetic anhydride (0.3 ml) and stirred for 4 h at room temperature. The solvent was removed by evaporation in vacuo. The residue was treated with ethyl acetate (50 ml) and washed with dilute hydrochloric acid (30 ml) followed by a 5% aqueous sodium bicarbonate solution. The ethyl acetate was dried over anhydrous magnesium sulphate. The magnesium sulphate was removed by filtration and the filtrate evaporated in vacuo. The residue was subjected to flash column chromatography eluting with ethyl acetate to afford an oil. The oil was dissolved in methanol (1 ml) and treated with sodium methoxide (0.5M solution in methanol, 0.05 ml) and stood at room temperature for 3 h. The mixture was neutralised with ion exchange resin (Amberlite IRC 50 (H$^+$). The resin was removed by filtration, and the filtrate evaporated in vacuo. The residue was dissolved in water and freeze dried to afford compound 2 as an amorphous solid (7 mg).

2.7. The corresponding 4'-cyanouridine can be prepared by deprotection of compound (xi).

The deprotection can be carried out as follows:

Compound (xi) (50 mg, 82 μmol) was dissolved in tetrahydrofuran, treated with tetrabutylammonium fluoride on silica then stirred for 16 h at room temperature. The reaction mixture was filtered through Hyflo Super Cel (Fluka, cat no. 56678), evaporated in vacuo, then purified by flash column chromatography on silica gel, eluting with dichloromethane/methanol/acetic acid/water (240:24:3:2) followed by dichloromethane/methanol/acetic acid/water (90:18:3:2). Product containing fractions were combined and evaporated. The residue was dissolved in methanol/water (5:1), treated with Duolite C225 ion exchange resin (H$^+$ form, BDH, cat. no. 56678) and stirred for 15 min. The resin was removed by filtration and the filtrate evaporated in vacuo to low volume. The product was collected by filtration and dried in vacuo to afford 4'-cyanouridine as a white crystalline solid (15 mg); mass spectrum m/z (ESI) 270 [M+H]$^+$.

EXAMPLE 3

Preparation of Compound 3 According to the Method of Scheme 3

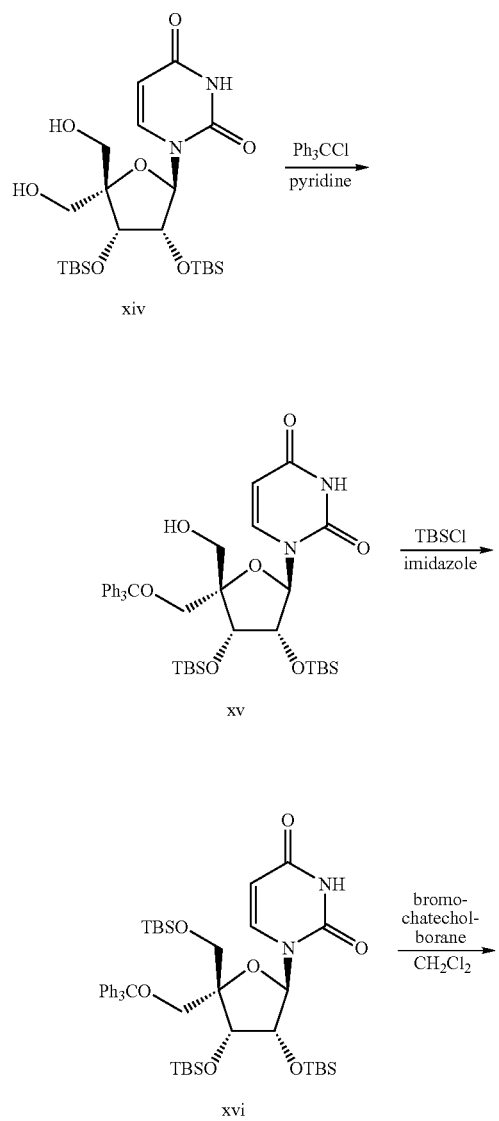

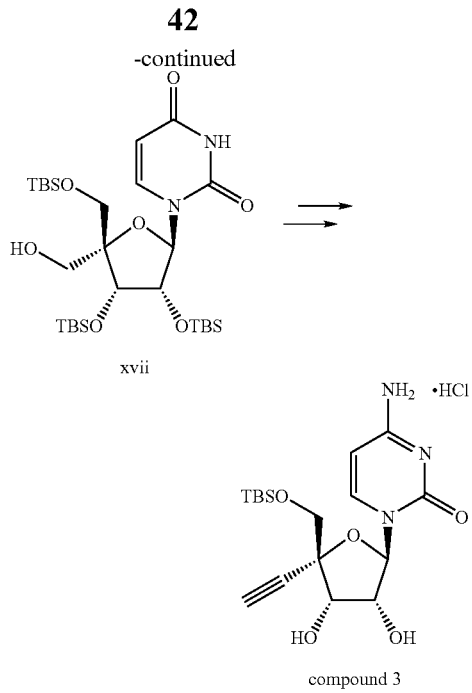

compound 3

3.1. Compound (xiv)

This compound was prepared as described by M. Nomura et al., J. Med. Chem., 1999, 42, 2901-2908.

3.2. Compound (xv)

Trityl chloride (3.2 g; 11.5 mmol) was added to a solution of compound (xiv) (3.0 g, 6.0 mmol) in pyridine (20 ml) and stirred at room temperature for 16 h. The solvent was evaporated in vacuo and the residue partitioned between ethyl acetate (50 ml) and 2 M hydrochloric acid (50 ml). The ethyl acetate layer was separated, washed with brine (50 ml) and dried over anhydrous magnesium sulphate. The magnesium sulphate was removed by filtration and the filtrate evaporated in vacuo. The crude material was purified by flash column chromatography on silica gel, eluting with 2:1 diethyl ether/hexane. Product containing fractions were combined and evaporated in vacuo to afford compound (xv) as a white solid (2.75 g); mass spectrum (ESI) m/z 767 [M+H]$^+$.

3.3. Compound (xvi)

tert-Butyldimethylsilylchloride (0.67 g, 4.4 mmol) and imidazole (0.91 g, 13.3 mmol) was added to a stirred solution of compound (xv) (2.75 g, 3.7 mmol) in dimethylformamide (20 ml). The reaction was heated to 45° C. for 16 h. Additional tert-butyldimethylsilylchloride (0.67 g, 4.4 mmol) and imidazole (0.91 g, 13.3 mmol) were added and the mixture was heated to 60° C. for 4 h. The solvent was removed by evaporation in vacuo and the residue was partitioned between ethyl acetate and brine. The ethyl acetate was separated and washed with more brine and dried over anhydrous magnesium sulphate. The magnesium sulphate was removed by filtration and the filtrate evaporated in vacuo. The residual colourless foam was purified by flash column chromatography on silica gel, eluting with 1:2 diethyl ether/hexane. Product containing fractions were combined and evaporated in vacuo to afford compound (xvi) as a white solid (3.1 g).

3.4. Compound (xvii)

Bromocatecholborane (355 mg, 1.77 mmol) was added to a stirred solution of compound (xvi) (1.5 g, 1.77 mmol) in dry dichloromethane (50 ml), under a nitrogen atmosphere at 0°

C. The reaction was stirred for 15 min, diluted with dichloromethane (50 ml) then washed with saturated sodium bicarbonate (100 ml) and brine (100 ml). The dichloromethane was dried over anhydrous magnesium sulphate. The magnesium sulphate was removed by filtration and the filtrate evaporated in vacuo. The residue was purified by flash column chromatography on silica gel, eluting with 1:1 diethyl ether/hexane. Product containing fractions were combined and evaporated in vacuo to afford compound (xvii) as a white solid (930 mg).

3.5. Compound 3 was prepared from compound (xvii) as described by M. Nomura et al., J. Med. Chem., 1999, 42, 2901-2908.

Further compounds can be prepared according to the methods described in the art, for example:

| Compound no. | Structure | Name and preparation method |
| --- | --- | --- |
| compound 6 | 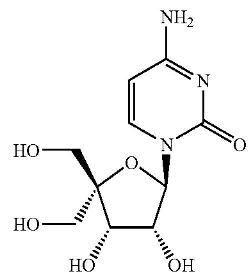 | 4'-C-(Hydroxymethyl)cytidine<br>G. H. Jones et al., J. Org. Chem., 1979, 44(8), 1309. |
| compound 7 | 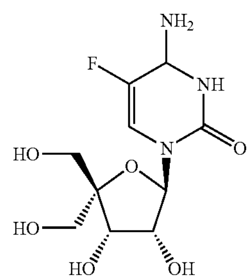 | 5-Fluoro-4'-C-(hydroxymethyl)uridine<br>Youssefyeh et al., J. Org. Chem., 1979, 44, 1301. |
| compound 8 | 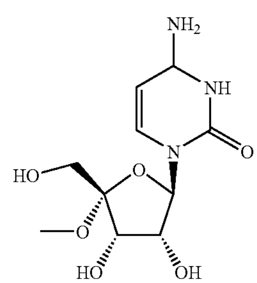 | 4'-C-Methoxyuridine<br>J. A. Cook and J. L. Secrost, J. Am. Chem. Soc., 1979, 101, 1554 |
| compound 9 | 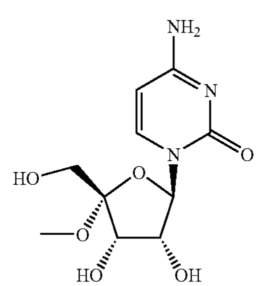 | 4'-C-Methoxycytidine<br>J. G. Moffatt and J. P. Verheyden, U.S. Pat. No. 3 910 885 |

| Compound no. | Structure | Name and preparation method |
|---|---|---|
| compound 22 | 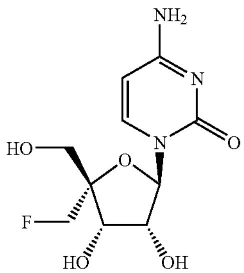 | 4'-C-(Fluoromethyl)cytidine<br>K. Kitano et al., Tetrahedron, 1997, 53(39), 13315. |
| compound 23 | 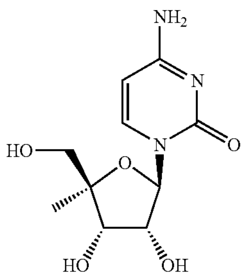 | 4'-C-Methylcytidine<br>T. Waga et al, J. Biosci. Biotechnol. Biochem., 1993, 57(9), 1433 |

Additional compounds of formula I can be prepared in analogy to the methods described in the prior art listed below:

| | |
|---|---|
| | 4'-C-Allyluridine<br>J. Secrist et al., J. Am. Chem. Soc., 1978, 100, 2554. |
| | 9-[4-C-(Hydroxymethyl)-beta-D-ribofuranosyl]-6-mercaptopurine<br>Youssefyeh et al., J. Org. Chem., 1979, 44, 1301 |
| | 4'-C-(Hydroxymethyl)adenosine<br>A. Rosenthal and M. Ratcliffe, Carbohydr. Res., 1977, 54, 61. |

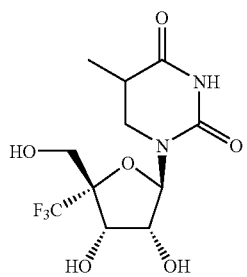
4'-C-(Trifluoromethyl)-5-methyluridine
J. Kozak and C. R. Johnson 1998, 17(12), 2221.
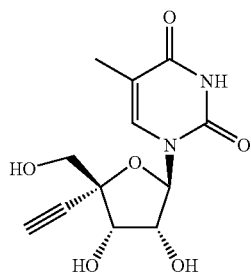
4'-C-(Ethynyl)-5-methyluridine
R. Yamaguchi et al., J. Biosci. Biotechnol. Biochem., 1999, 63(4), 736
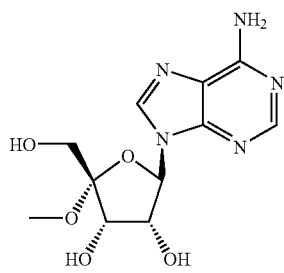
4'-C-Methoxyadenosine
C. M. Richards et al., Carbohydr. Res., 1982, 100, 315.
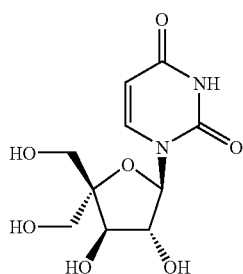
1-[4-C-(Hydroxymethyl)-beta-D-xylofuranosyl]uracil
G. H. Jones et al., J. Org. Chem., 1979, 44(8), 1309-1317
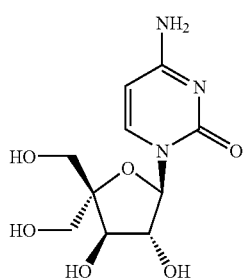
1-[4-C-(Hydroxymethyl)-beta-D-arabinofuranosyl]cytosine
T. Waga et al., Nucleosides Nucleotides, 1996, 15(1-3) 287-304

-continued

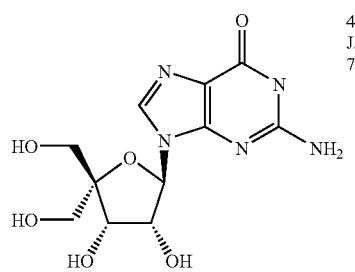

4'-C-(Hydroxymethyl)guanosine
J. C. Martin and J. P. Verheyden, Nucleosides Nucleotides 1988, 7(3), 365

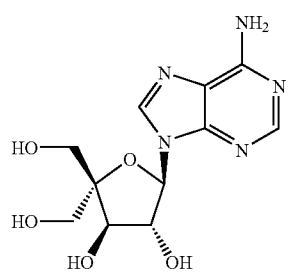

9-[4-C-(Hydroxymethyl)-beta-D-xylofuranosyl]adenine
D. L. Leland and M. P. Kotick, Carbohydr. Res., 1974, 38, C9-C11

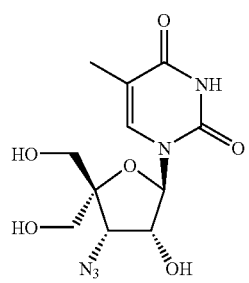

3'-Azido-3'-deoxy-4'-C-(hydroxymethyl)-5-methyluridine
A. G. Olsen et al, J. Chem. Soc. Perkin Trans. 1, 2000, 21, 3610

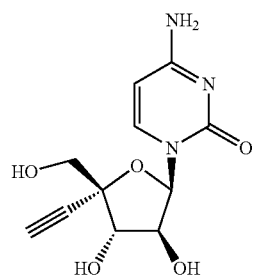

1-(4-C-Ethynyl-beta-D-arabinofuranosyl)cytosine
H. Ohrui et al, J. Med. Chem., 2000, 43(23), 4516 or S. Kohgo et al., Biosci. Biotechnol. Biochem., 1999, 63(6), 1146

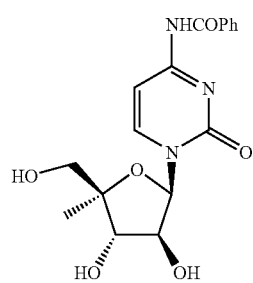

N4-Benzoyl-1-[4-C-methyl-beta-D-arabinofuranosyl]cytosine
T. Yamaguchi et al., Nucleosides Nucleotides, 1997, 16(7), 1347

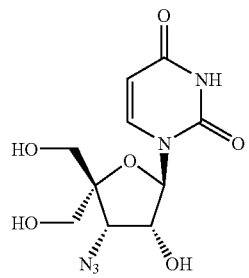

3'-Azido-3'-deoxy-4'-C-(hydroxymethyl)uridine
S. A. Surzhikov and N. B. Dyatkina Russ. J. Biorg. Chem. (Engl. Transl.), 1993, 19(7), 408

The following assay method demonstrates the ability of the compounds of formula I to inhibit HCV RNA replication, and therefore their potential utility for the treatment of HCV infections.

Renilla Luciferase Assay

This assay is based on the idea of using a reporter as a simple readout for intracellular HCV replicon RNA level. For this purpose Renilla luciferase gene was introduced into the first open reading frame of a replicon construct NK5.1 (Krieger et al., J. Virol. 75:4614), immediately after the internal ribosome entry site (IRES) sequence, and fused with the neomycin phosphotransferase (NPTII) gene via a self-cleavage peptide 2A from foot and mouth disease virus (Ryan & Drew, EMBO Vol 13:928-933). After in vitro transcription the RNA was electroporated into human hepatoma Huh7 cells, and G418-resistant colonies were isolated and expanded. Stably selected cell line 2209-23 was shown to contain replicative HCV subgenomic RNA, and the activity of Renilla luciferase expressed by the replicon reflects its RNA level in the cells.

For the assay procedure, Renilla Luciferase HCV replicon cells (2209-23) that cultured in Dulbecco's MEM (Gibco-BRL cat no. 31966-021) with 5% fetal calf serum (FCS, GibcoBRL cat. no. 10106-169) were plated onto a 96-well plate at 5000 cells per well, and incubated overnight. Twenty-four hours later, different dilutions of chemical compounds in the growth medium were added to the cells, which were then further incubated at 37° C. for three days. The assay was carried out in duplicate plates, one in opaque white and one in transparent, in order to measure the activity and cytotoxicity of a chemical compound in parallel ensuring the activity seen is not due to reduction on cell proliferation.

At the end of the incubation time, the cells in white plates were harvested and luciferase activity was measured by using Dual-Luciferase reporter assay system (Promega cat no. E1960) All the reagents described in the following paragraph were included in the manufacturers kit, and the manufacturer's instructions were followed for preparations of the reagents. Briefly, the cells were washed twice with 200 µl phosphate buffered saline (pH 7.0) (PBS) per well and lysed with 25 µl of 1× passive lysis buffer prior to incubation at room temperature for 20 min. One hundred microlitre of LAR II reagent was added to each well. The plate was then inserted into the LB 96V microplate luminometer (MicroLumatPlus, Berthold), and 100 µl of Stop & Glo reagent was injected into each well by the machine and the signal measured using a 2-second delay, 10-second measurement program. IC50, the concentration of the drug required for reducing replicon level by 50% in relation to the untreated cell control value, can be calculated from the plot of percentage reduction of the luciferase activity vs. drug concentration. The results are compiled below.

For the cytotoxicity assay, WST-1 reagent from Roche Diagnostic (cat no. 1644807) was used. Ten microlitre of WST-1 reagent was added to each well including wells that contain media alone as blanks. Cells were then incubated for 1 to 1.5 hours at 37° C., and the OD value was measured by a 96-well plate reader at 450 nm (reference filter at 650 nm). Again CC50, the concentration of the drug required for reducing cell proliferation by 50% in relation to the untreated cell control value, can be calculated from the plot of percentage reduction of the WST-1 value vs. drug concentration.

| Compound no. | STRUCTURE | Name | IC50 (µM) | CC50 (µM) WST-1 |
|---|---|---|---|---|
| compound 1 | ![structure] | 4'-C-Azidocytidine | 1.2 | 0% (100 µM) |

-continued

| Compound no. | STRUCTURE | Name | IC50 (μM) | CC50 (μM) WST-1 |
|---|---|---|---|---|
| compound 3 | (structure shown) | 4'-C-Ethynylcytidine hydrochloride (1:1) | 3% (20 μM) | 0% (20 μM) |

As shown in above Table the compounds of formula I have the potential to be efficacious as antiviral drugs for the treatment of HCV infections in humans, or are metabolized to a compound that exhibit such activity.

In another embodiment of the invention, the active compound or its derivative or salt can be administered in combination with another antiviral agent, such as an anti-hepatitis agent, including those of formula I. When the active compound or its derivative or salt are administered in combination with another antiviral agent the activity may be increased over the parent compound. This can easily be assessed by preparing the derivative and testing its anti-HCV activity according to the method described herein.

Administration of the active compound may range from continuous (intravenous drip) to several oral administrations per day (for example, Q.I.D) and may include oral, topical parenteral, intramuscular, intravenous, subcutaneous, transdermal (which may include a penetration enhancement agent), buccal and suppository administration, among other routes of administration.

The 4'-substituted nucleoside derivatives as well as their pharmaceutically useable salts, can be used as medicaments in the form of any pharmaceutical formulation. The pharmaceutical formulation can be administered enterally, either orally, e.g. in the form of tablets, coated tablets, dragées, hard and soft gelatine capsules, solutions, emulsions, syrups, or suspensions, or rectally, e.g. in the form of suppositories. They can also be administered parenterally (intramuscularly, intravenously, subcutaneously or intrasternal injection or infusion techniques), e.g. in the form of injection solutions, nasally, e.g. in the form of nasal sprays, or inhalation spray, topically and so forth.

For the manufacture of pharmaceutical preparations, the 4'-substituted nucleoside derivatives, as well as their pharmaceutically useable salts, can be formulated with a therapeutically inert, inorganic or organic excipient for the production of tablets, coated tablets, dragées, hard and soft gelatine capsules, solutions, emulsions or suspensions.

The compounds of formula I can be formulated in admixture with a pharmaceutically acceptable carrier. For example, the compounds of the present invention can be administered orally as pharmacologically acceptable salts. Because the compounds of the present invention are mostly water soluble, they can be administered intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the ordinary skill of the art to modify the route of administration and dosage regimen of a particular compound in order to manage the pharmacokinetics of the present compounds for maximum beneficial effect in patients.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Suitable excipients for tablets, coated tablets, dragées, and hard gelatin capsules are, for example, lactose, corn starch and derivatives thereof, talc, and stearic acid or its salts.

If desired, the tablets or capsules may be enteric-coated or sustained release by standard techniques.

Suitable excipients for soft gelatine capsules are, for example, vegetable oils, waxes, fats, semi-solid and liquid polyols.

Suitable excipients for injection solutions are, for example, water, saline, alcohols, polyols, glycerine or vegetable oils.

Suitable excipients for suppositories are, for example, natural and hardened oils, waxes, fats, semi-liquid or liquid polyols.

Suitable excipients for solutions and syrups for enteral use are, for example, water, polyols, saccharose, invert sugar and glucose.

The pharmaceutical preparations of the present invention may also be provided as sustained release formulations or other appropriate formulations.

The pharmaceutical preparations can also contain preservatives, solubilizers, stabilizers, wetting agents, emulsifiers, sweeteners, colorants, flavourants, salts for adjustment of the osmotic pressure, buffers, masking agents or antioxidants.

The pharmaceutical preparations may also contain other therapeutically active agents known in the art.

The dosage can vary within wide limits and will, of course, be adjusted to the individual requirements in each particular case. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 100 mg/kg body weight per day. A typical preparation will contain from about 5% to about 95% active compound (w/w). The daily dosage can be administered as a single dosage or in divided dosages, typically between 1 and 5 dosages per day.

In certain pharmaceutical dosage forms, the pro-drug form of the compounds, especially including acylated (acetylated or other) derivatives, pyridine esters and various salt forms of the present compounds are preferred. One of ordinary skill in the art will recognise how to readily modify the present compounds to pro-drug forms to facilitate delivery of active compounds to a target site within the host organism or patient. One of ordinary skill in the art will also take advantage of favourable pharmacokinetic parameters of the pro-drug forms, where applicable, in delivering the present compounds to targeted site within the host organism or patient to maximise the intended effect of the compound.

The nucleoside derivatives or the medicaments thereof may be used in monotherapy or combination therapy, i.e. the treatment may be in conjunction with the administration of one or more additional therapeutically active substance(s), for example, an immune system modulator such as an interferon, interleukin, tumor necrosis factor or colony stimulating factor; an antiviral agent or an anti-inflammatory agent. When the treatment is combination therapy, such administration may be concurrent or sequential with respect to that of the 4'-substituted nucleoside derivatives. Concurrent administration, as used herein thus includes administration of the agents at the same time or at different times.

It will be understood that references herein to treatment extend to prophylaxis as well as to the treatment of existing conditions, and that the treatment of animals includes the treatment of humans as well as other mammals. Furthermore, treatment of an Hepatitis C Virus (HCV) infection, as used herein, also includes treatment or prophylaxis of a disease or a condition associated with or mediated by Hepatitis C Virus (HCV) infection, or the clinical symptoms thereof.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound according to formula Ia wherein:

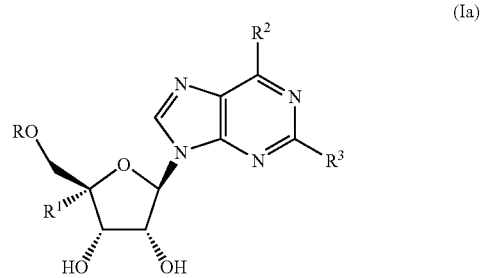

the compound is in the D configuration, and;
R is hydrogen or —[P(O)(OH)]—O]$_n$H and n is 1, 2 or 3
R$^1$ is —N$_3$, or C$_{3-6}$ alkynyl;
R$^2$ and R$^3$ are independently hydrogen, —OH or —NR$^4$$_2$;
R$^4$ is hydrogen or C$_{1-3}$ alkyl; or,
a pharmaceutically acceptable salt thereof.

2. A pharmaceutical composition comprising a compound according to claim 1 admixed with at least one carrier, diluent or excipient.

* * * * *